United States Patent
Huan et al.

(10) Patent No.: US 11,771,672 B2
(45) Date of Patent: Oct. 3, 2023

(54) USE OF 2-HYDROXYOLEIC ACID FOR THE TREATMENT OF SYSTEMIC LUPUS ERYTHEMATOSUS AND OTHER IMMUNE PATHOLOGIES

(71) Applicant: THE RESEARCH FOUNDATION FOR THE STATE UNIVERSITY OF NEW YORK, Albany, NY (US)

(72) Inventors: Chongmin Huan, Brooklyn, NY (US); Christopher Roman, Brooklyn, NY (US); Peiqi Ou, Brooklyn, NY (US)

(73) Assignee: THE RESEARCH FOUNDATION FOR THE STATE UNIVERSITY OF NEW YORK, Albany, NY (US)

(*) Notice: Subject to any disclaimer, the term of this patent is extended or adjusted under 35 U.S.C. 154(b) by 0 days.

(21) Appl. No.: 16/760,146

(22) PCT Filed: Nov. 15, 2018

(86) PCT No.: PCT/US2018/061274
§ 371 (c)(1),
(2) Date: Apr. 29, 2020

(87) PCT Pub. No.: WO2019/099664
PCT Pub. Date: May 23, 2019

(65) Prior Publication Data
US 2020/0330419 A1 Oct. 22, 2020

Related U.S. Application Data

(60) Provisional application No. 62/587,274, filed on Nov. 16, 2017.

(51) Int. Cl.
*A61K 31/201* (2006.01)
*A61P 37/02* (2006.01)
*A61K 9/00* (2006.01)

(52) U.S. Cl.
CPC .......... *A61K 31/201* (2013.01); *A61K 9/0053* (2013.01); *A61P 37/02* (2018.01)

(58) Field of Classification Search
CPC ...... A61K 31/201; A61K 9/0053; A61P 37/02
See application file for complete search history.

(56) References Cited

U.S. PATENT DOCUMENTS

| 9,359,281 B2 | 6/2016 | Escriba Ruiz et al. | |
| 9,730,906 B2 | 8/2017 | Escriba Ruiz et al. | |
| 2002/0058029 A1 | 5/2002 | Hanna | |
| 2011/0294883 A1* | 12/2011 | Escriba Ruiz | A61P 25/16 |
| | | | 514/560 |
| 2014/0288176 A1 | 9/2014 | Escriba Ruiz et al. | |

OTHER PUBLICATIONS

Leslie et al. J. Clin. Investig. 2001, 108 (1), 1417-1422.*
Health John Hopkins Medicine https://www.hopkinsmedicine.org/health/wellness-and-prevention/what-are-common-symptoms-of-autoimmune-disease, downloaded May 12, 2021.*
Dema et al. Antibodies 2016, 5, 2, doi:10.3390/antib5010002, p. 1-32.*
Sticherling et al. J. Deutsche Dermatologische Gesellschaft (Journal of the German Society of Dermatology) JDDG2008, 6, 48-61.*
Liang et al. Immunology 2006, 119, 296-305.*
International Search Report and Written Opinion of the International Searching Authority for International Application No. PCT/US2018/061274 dated Feb. 1, 2019.
Alemany, R., et al., "Antihypertensive action of 2-hydroxyoleic acid in SHRs via modulation of the protein kinase A pathway and Rho kinase," Journal of Lipid Research, vol. 47, pp. 1762-1770 (2006).
Chan, V.S. et al., "B-cell-targeted therapies in systemic lupus erythematosus", Cellular & Molecular Immunology, vol. 10, pp. 133-142 (2013).
Martinez, J., et al., "Membrane Structure Modulation, Protein Kinase Cα Activation, and Anticancer Activity of Minerval", Molecular Pharmacology, vol. 67, No. 2, pp. 531-540 (2005).
Nashi, E., et al., "The Role of B Cells in Lupus Pathogenesis", Int J Biochem Cell Biol., vol. 42, No. 4, pp. 543-550 (2010).
Piotto, S., et al., "Differential effect of 2-hydroxyoleic acid enantiomers on protein (sphingomyelin synthase) and lipid (membrane) targets", Biochimica et Biophysica Acta, vol. 1838, pp. 1628-1637 (2014).
Roda, D., et al., "A first-in human dose-escalation study of the safety, pharmacokinetics (PK), and pharmacodynamics (PD) of oral 2-hydroxyoleic acid (2-OHOA) in adult patients (pt) with advanced solid tumors including grade III/IV glioblastoma multiforme (GBM)", Journal of Clinical Oncology, vol. 33, No. 15 Suppl, pp. 2513 (2015).
Torgersen, M.L., et al., "The anti-tumor drug 2-hydroxyoleic acid (Minerval) stimulates signaling and retrograde transport", Oncotarget, vol. 7, No. 52, pp. 86871-86888 (2016).
Vogler, O., et al., "Structure-effect relation of C18 long-chain fatty acids in the reduction of body weight in rats", International Journal of Obesity, vol. 32, pp. 464-473 (2008).
Azaro et al., "Final report of a phase I study of 2-hydroxyloeic acid (2OHOA), a novel sphingomyelin synthase activator in patients (pt) with advance solid tumors (AST) including recurrent high grade glimoas (rHGG)," ASCO Annual Meeting, Jun. 2017, Poster #2554.
Terés et al., "2-Hydroxyoleate, a nontoxic membrane binding anticancer drug, induces glioma cell differentiation and autophagy," PNAS, May 2012, 109(2):8489-8494.

(Continued)

Primary Examiner — Irina Neagu
(74) Attorney, Agent, or Firm — HESLIN ROTHENBERG FARLEY & MESITI P.C.

(57) ABSTRACT

Provided is a method of reducing autoimmunity, including reducing an amount of self-reactive B cells in a subject expressing elevated levels of an autoantibody, wherein reducing includes administering 2-hydroxyoleic acid to the subject. Also provided is a method of treatment including administering 2-hydroxyoleic acid to a subject expressing elevated levels of an auto-antibody. Also provided is a method of promoting B cell tolerance, including promoting apoptosis of self-reactive B cells in a subject, wherein promoting includes administering 2-hydroxyoleic acid to the subject.

14 Claims, 25 Drawing Sheets

(56) References Cited

OTHER PUBLICATIONS

Barcelo-Coblijn et al., "Sphingomyelin and sphingomyelin synthase (SMS) in the malignant transformation of glioma cells and in 2-hydroxyloeic acid therapy," PNAS, Dec. 2011, 108(49): 19569-19574.

Huan et al., "Transcription factors TFE3 and TFEB are critical for CD40 ligand expression and thymus-dependent humoral immunity," Nature Immunology, Oct. 2006, 7(10):1082-1091.

Ou et al., "SMS2 deficiency impairs PKCδ-regulated B cell tolerance in the germinal center," Cell Reports, Aug. 2021, 36(9)109624.

Liu et al., "Macrophage Sphingomyelin Synthase 2 Deficiency Decreases Atherosclerosis in Mice," Circulation Research, Jul. 2009, 105(3):295-303.

Ablynx, "Ablynx Announces Topline Results from the Phase II Study of Vobarilizumab in Patients with Systemic Lupus Erythematosus," Mar. 2018.

Pocock et al., "Subgroup analysis, covariate adjustment and baseline comparisons in clinical trial reporting: current practice and problems," Statistics in Medicine, 2002, 21:2917-2930.

Misra, "Randomized double blind placebo control studies, the "Gold Standard" in intervention based studies," Indian Journal of Sexually Transmitted Diseases and AIDS, 2012, 33(2):131-134.

Wallace et al., "Efficacy and safety of an interleukin 6 monoclonal antibody for the treatment of systemic lupus erythematosus: a phase II dose-ranging randomised controlled trial," Annals of the rheumatic diseases, Mar. 2017, 76(3):534-542.

Rovin et al., "A Multicenter, Randomized, Double-Blind, Placebo-Controlled Study to Evaluate the Efficacy and Safety of Treatment With Sirukumab (CNTO 136) in Patients With Active Lupus Nephritis," Arthritis & Rheumatology, Sep. 2016, 68(9):2174-2183.

Choy et al., "Translating IL-6 biology into effective treatments," Nature Review Rheumatology, Jun. 2020, 16:335-345.

\* cited by examiner

USE OF 2-HYDROXYOLEIC ACID FOR THE TREATMENT OF SYSTEMIC LUPUS ERYTHEMATOSUS AND OTHER IMMUNE PATHOLOGIES

CROSS REFERENCE TO RELATED APPLICATIONS

This application is a national stage filing under 35 U.S.C. § 371 of International Application No. PCT/US2018/061274, filed on Nov. 15, 2018, published as WO 2019099664 on May 23, 2019, and claims priority to U.S. Provisional Patent Application 62/587,274, filed Nov. 16, 2017. The entire contents of the said applications are incorporated herein by reference.

FIELD OF THE INVENTION

The present disclosure related to treatments for conditions affecting immune system function. More particularly, disclosed herein are compositions and methods for reducing self-reactive B cells or autoantibodies in an individual in need of such reducing, such as an individual diagnosed with lupus erythematosus or another autoimmune disorder, including by administering to such individual 2-hydroxyoleic acid.

BACKGROUND OF THE INVENTION

Autoimmune diseases such as systemic lupus erythematosus (SLE), rheumatoid arthritis, and pemphigus vulgaris are severe autoimmune diseases resulting from tissue injury caused by pathogenic autoantibodies against self molecules such as DNA. Autoantibodies are antibodies produced by one's immune system that pathologically recognize and bind to biomolecules produced by one's own body, triggering a pathological response of one's immune system against one's own cells or tissue. Treatments for such debilitating diseases are of limited availability and effectiveness. It is therefore desirable to develop an improved treatment.

The random nature in the genetic modification of the genes encoding immunoglobulin (Ig) enables B cells to recognize and respond to an apparently limitless array of pathogens, but also undesirably renders some B cells self-reactive. B cell tolerance mechanisms are in place to delete or deactivate naturally arising self-reactive B cells to prevent the production of self-reactive Igs. B cell tolerance refers to the normal process whereby potentially self-reactive, autoantibody production is recognized by the immune system and the cells that are the source of potentially self-reactive autoantibodies are cleared, or removed, from the body thereby eliminating the source of the pathological autoantibodies that may otherwise result. Deletion of self-reactive B cell has been observed in the germinal center (GC) where somatic hypermutation (SHM) in Ig genes' variable regions can potentially endow B cells with higher-affinity Igs to foreign antigens, and with Igs that recognize self-antigens. Failed clearance of these self-reactive B cells that arise in the GC has been considered as a major source of autoimmunity in autoimmune disorders such as SLE, which is characterized by anti-double stranded (ds) DNA IgG. Thus, a method to improve or correct poor clearance of self-reactive B cells and thereby enhance B cell tolerance is desirable as a potential treatment for certain autoimmune disorders, including SLE, rheumatoid arthritis, and pemphigus vulgaris.

SUMMARY OF THE INVENTION

Disclosed is a method of reducing autoimmunity, including reducing an amount of self-reactive B cells in a subject expressing elevated levels of an autoantibody, wherein reducing includes administering 2-hydroxyoleic acid to the subject. In an aspect, the subject may be a human subject exhibiting symptoms of an autoimmune disease. For example, the autoimmune disease may be SLE. In another aspect, administration may include oral administration. In still another aspect, the auto-antibody may be an anti-nuclear antigen antibody. For example, the anti-nuclear antigen antibody may be an anti-DNA antibody. In another aspect, the subject may be a non-human mammal. In still another aspect, the method may further include administering a second compound to the subject, where the second compound may include an immunosuppressant compound, a corticosteroid, a non-steroidal anti-inflammatory compound, an anti-malarial compound, an anti-B-cell-specific surface antigen antibody, an anti-B cell activating factor antibody, or any combination of two or more of the foregoing.

In another embodiment, disclosed is a method of treatment including administering 2-hydroxyoleic acid to a subject expressing elevated levels of an auto-antibody. In an aspect, the subject may exhibit symptoms of SLE. In another aspect, administering includes oral administration. In another aspect, the subject may be a human subject diagnosed with SLE. In yet another aspect, the subject may be a human subject diagnosed with lupus nephritis. In some examples, the method may further include administering a second compound to the subject and the second compound may be an immunosuppressant compound, a corticosteroid, a non-steroidal anti-inflammatory compound, an anti-malarial compound, an anti-B-cell-specific surface antigen antibody, an anti-B cell activating factor antibody, or any combination of two or more of the foregoing.

In a still further embodiment, disclosed is a method of promoting B cell tolerance, including promoting apoptosis of self-reactive B cells in a subject, wherein promoting includes administering 2-hydroxyoleic acid to the subject. In an aspect, the subject may exhibit elevated levels of an autoantibody. In another aspect, the subject may exhibit symptoms of systemic lupus erythematosus. In yet another aspect, the subject may exhibit elevated levels of an autoantibody. For example, the subject may exhibit elevated levels of an anti-DNA antibody. In a still further aspect, the method may further include administering a second compound to the subject and the second compound is selected from an immunosuppressant compound, a corticosteroid, a non-steroidal anti-inflammatory compound, an anti-malarial compound, an anti-B-cell-specific surface antigen antibody, an anti-B cell activating factor antibody, or any combination of two or more of the foregoing.

BRIEF DESCRIPTION OF THE DRAWINGS

These and other features, aspects, and advantages of the invention disclosed herein will become better understood when the following detailed description is read with reference to the accompanying drawings, wherein.

DETAILED DESCRIPTION OF THE INVENTION

Figure 1A:
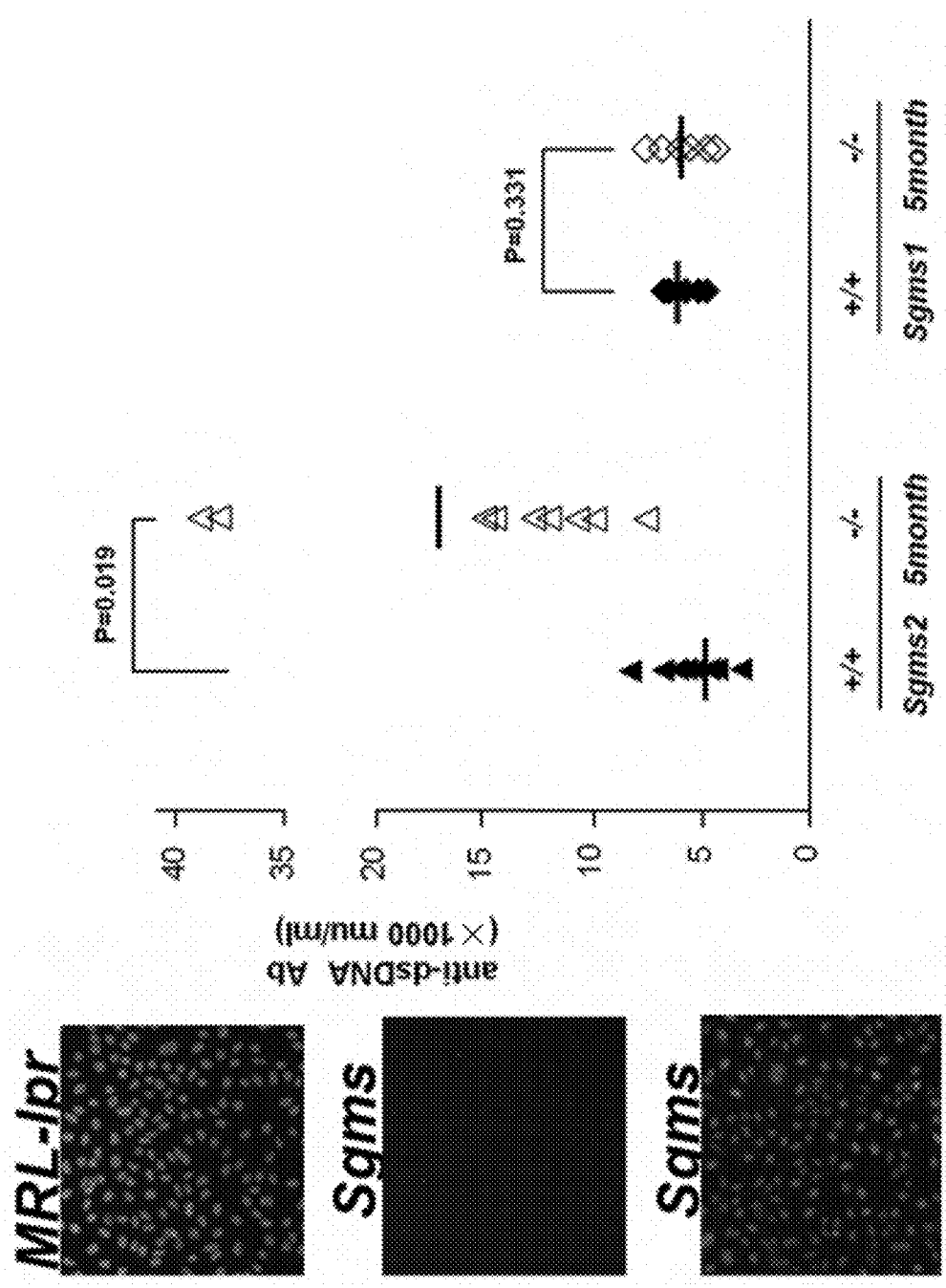
FIG. 1A shows photomicrographic (left panel) and graphical (right panel) evidence of increased serum anti-nuclear antibodies (ANA) in sphingomyelin synthase 2 homozygous knockout mice (Sgms2$^{-/-}$).

Aspects of an invention disclosed herein and certain features, advantages, and details thereof, are explained more fully below with reference to the non-limiting embodiments illustrated in the accompanying drawings. Descriptions of well-known materials, fabrication tools, processing techniques, etc., are omitted so as to not unnecessarily obscure the invention in detail. It should be understood, however, that the detailed description and the specific examples, while indicating some embodiments, are given by way of illustration only, and are not by way of limitation. Various substitutions, modifications, additions and/or arrangements within the spirit and/or scope of the underlying inventive concepts will be apparent to those skilled in the art from this disclosure.

The invention disclosed herein relates to inter alia treatments for conditions affecting immune system function. Surprisingly, as disclosed herein, sphingomyelin synthase 2 (SMS2) homozygous knockout mice (Sgms2$^{-/-}$), genetically engineered to lack expression of the sphingomyelin synthase 2 protein, exhibit symptoms of autoimmune pathology (for example, SLE). Also surprisingly, as further disclosed herein, 2-hydroxyoleic acid (2OHOA), an activator of SMS activity, reverses pathophysiological indicia of autoimmune disorders. Because reduction of SMS2 activity increases indicia of autoimmune disorders including SLE, and stimulation of SMS2 activity with 2OHOA ameliorates such indicia, the present disclosure indicates that methods that increase activity of SMS2, such as 2OHOA, may be used to protect against or treat autoimmune pathophysiology.

Disclosed is a method of reducing autoimmunity, including reducing an amount of self-reactive B cells in a subject expressing elevated levels of an autoantibody, wherein reducing includes administering 2-hydroxyoleic acid to the subject. In an aspect, the subject may be a human subject exhibiting symptoms of an autoimmune disease. For example, the autoimmune disease may be SLE. In another aspect, administration may include oral administration. In still another aspect, the auto-antibody may be an anti-nuclear antigen antibody. For example, the anti-nuclear antigen antibody may be an anti-DNA antibody. In another aspect, the subject may be a non-human mammal. In still another aspect, the method may further include administering a second compound to the subject, where the second compound may include an immunosuppressant compound, a corticosteroid, a non-steroidal anti-inflammatory compound, an anti-malarial compound, an anti-B-cell-specific surface antigen antibody, an anti-B cell activating factor antibody, or any combination of two or more of the foregoing.

In another embodiment, disclosed is a method of treatment including administering 2-hydroxyoleic acid to a subject expressing elevated levels of an auto-antibody. In an aspect, the subject may exhibit symptoms of SLE. In another aspect, administering includes oral administration. In another aspect, the subject may be a human subject diagnosed with SLE. In yet another aspect, the subject may be a human subject diagnosed with lupus nephritis. In some examples, the method may further include administering a second compound to the subject and the second compound may be an immunosuppressant compound, a corticosteroid, a non-steroidal anti-inflammatory compound, an anti-malarial compound, an anti-B-cell-specific surface antigen antibody, an anti-B cell activating factor antibody, or any combination of two or more of the foregoing.

In a still further embodiment, disclosed is a method of promoting B cell tolerance, including promoting apoptosis of self-reactive B cells in a subject, wherein promoting includes administering 2-hydroxyoleic acid to the subject. In an aspect, the subject may exhibit elevated levels of an autoantibody. In another aspect, the subject may exhibit symptoms of systemic lupus erythematosus. In yet another aspect, the subject may exhibit elevated levels of an autoantibody. For example, the subject may exhibit elevated levels of an anti-DNA antibody. In a still further aspect, the method may further include administering a second compound to the subject and the second compound is selected from an immunosuppressant compound, a corticosteroid, a non-steroidal anti-inflammatory compound, an anti-malarial compound, an anti-B-cell-specific surface antigen antibody, an anti-B cell activating factor antibody, or any combination of two or more of the foregoing.

Numerous autoimmune disorders are known or believed to result from aberrations in processes related to the generation, development, and maturation of B cells in the GC. For example, the process of B-cell tolerance involves the elimination of B cells that produce antibodies that bind with an individual's own antigens with a sufficient affinity to trigger an immune response directed to such antigens or cells or tissue that contain or express them, so-called self-reactive antibodies or autoantibodies. If the process by which autoantibodies are produced and normally removed during the generation of B cells fails to function properly, B cells producing autoantibodies may develop to maturity and result in the production of autoantibodies in sufficient levels to cause various autoimmune diseases, or the detection of which signifies that an individual is exhibiting signs consistent with diagnosis with a given autoimmune disease. Conditions which do or are believed to result from ineffective GC B cell tolerance mechanisms include SLE, rheumatoid arthritis, and pemphigus vulgaris.

Disclosed herein is a method of preventing, reducing, ameliorating, or inhibiting the generation, development, or maturation of B-cells that produce autoantibodies. In some examples, the method may include preventing creation, or enhancing elimination, of B cells that produce autoantibodies, or otherwise preventing or reducing the generation or presence of autoantibodies in an individual. In other examples, the method may include treatment of symptoms of a disease, condition, syndrome, or disorder, or ill health effects, that are or are believed to be related to, caused by, or exacerbated by presence of autoantibodies. In still other examples, disclosed is a method of promoting apoptosis of self-reactive B-cells to prevent their maturation and survival which would result in generation of self-reactive antibodies in an individual.

More particularly, disclosed is a method of administering a compound 2-hydroxyoleic acid (2OHOA), or a pharmaceutically acceptable salt thereof. Without being limited to any particular mechanism of action, is believed that 2OHOA promotes activity of the enzyme SMS2. Still without being limited to any particular mechanism of action, it is further believed that increased activity of SMS2 stimulates activity of the kinase PKCδ, which in turn promotes apoptosis of B cells that produce self-reactive antibodies (that is, promotes B-cell tolerance).

In some examples, 2OHOA can exist as distinct stereoisomers, or as a racemic mixture of stereoisomers. As disclosed in U.S. Pat. No. 935,928, particular stereoisomers of 2OHOA, or particular racemic mixtures, may differentially stimulate activity of SMS. On the basis of the present disclosure, such isolated stereoisomers, or racemic mixtures, may likewise have differential effects on autoimmune disorders such as SLE, rheumatoid arthritis, pemphigus vulgaris, or others. For example, stereoisomer (S)-2-hydroxyoleic acid (which corresponds to the (−) optical stereoisomer), or pharmaceutically acceptable salts thereof, may be used in place of racemic 2OHOA as disclosed herein, given that (S)-2OHOA more strongly stimulates SMS activity than (R)-2-hydroxyoleic acid (which corresponds to the (+) optical stereoisomer) or a mixture of the two stereoisomers.

Unless otherwise specified, use of the term "2OHOA" or "2-hydroxyoleic acid" herein refers to mixtures of stereoisomers of 2OHOA. In other instances, (S)-2OHOA may exist in a pure form. Mixtures of (S)- with (R)-2OHOA may exist containing less than 50%, 50% or more, 55% or more, 60% or more, 65% or more, 70% or more, 75% or more, 80% or more, 85% or more, 90% or more, 95% or more, 97% or more, 99% or more, or 99.9% or more by weight of (S)-2OHOA, and any and all of the foregoing mixtures may be used in any manner disclosed herein as a use for 2OHOA, as may pure (S)-2OHOA. Any and all such uses of any and all of the foregoing mixtures of stereoisomers, and pure (S)-2OHOA, or pharmaceutically acceptable salts thereof, are explicitly included in the present disclosure.

As is also known, as disclosed in U.S. Pat. No. 9,359,281, is addition to 2OHOA, other compounds stimulate SMS activity. Examples of such compounds include 2-hydroxylinoleic acid, 2-hydroxy-gamma-linoleic acid, and 2-hydroxy-alpha-linoleic acid, and 2-hydroxypalmitoleic acid. Just as 2OHOA, as disclosed herein, any one or more of the foregoing compounds, alone or in combination, or pharmaceutically acceptable salts thereof, may be used for treatment of autoimmune diseases, such as SLE, rheumatoid arthritis, pemphigus vulgaris, or others. Other examples of such compounds include compounds of Formula I:

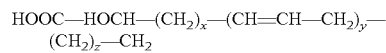

where x, y, and z are each independently integers of between 0 and 6, inclusively, and the total number of carbon atoms in such compound of Formula I does not exceed 20. Compounds of Formula I stimulate SMS activity. Compounds of Formula I may also be used for the treatment of autoimmune disorders, such as SLE, rheumatoid arthritis, or pemphigus vulgaris, or others, in accordance with the present disclosure.

As with (S)-2OHOA, (S)-stereoisomers (which are (−) stereoisomers) of any and all of the foregoing compounds (for example, 2-hydroxylinoleic acid, 2-hydroxy-gamma-linoleic acid, and 2-hydroxy-alpha-linoleic acid, 2-hydroxypalmitoleic acid, or compounds of Formula I), or combinations of two or more thereof, or pharmaceutically acceptable salts thereof, may also be used in any manner for which a use of 2-OHOA is disclosed herein. (S) stereoisomers of any and all of the foregoing (which corresponds to the (−) optical stereoisomer), may be used in place of racemic mixtures 2OHOA or of other of the foregoing compounds such as of Formula I, as disclosed herein, whereas such (S)-stereoisomers may more strongly stimulate SMS activity than corresponding (R)-stereoisomers or mixtures of stereoisomers. Mixtures of (S)- and (R)-stereoisomers of such compounds may exist containing less than 50%, 50% or more, 55% or more, 60% or more, 65% or more, 70% or more, 75% or more, 80% or more, 85% or more, 90% or more, 95% or more, 97% or more, 99% or more, or 99.9% or more by weight of (S)-stereoisomer, and any and all of the foregoing mixtures may be used in any manner disclosed herein as a use for 2OHOA, as may pure (S)-stereoisomers thereof. Any and all such uses of any and all of the foregoing mixtures of stereoisomers, and pure (S)-stereoisomers, or pharmaceutically acceptable salts thereof, or any and all combinations of any two or more of any of the foregoing, are explicitly included in the present disclosure.

SLE symptoms may differ from individual to individual, or temporally or in severity within the same individual depending on many factors, including what organ or tissue is being affected. Symptoms may include fatigue, joint pain or swelling, headaches, skin rash or a facial rash, loss of hair, anemia, complications in blood clotting processes, tingling or turning white of fingers or toes when cold, or other symptoms of the digestive tract, heart, or skin. SLE may include production of anti-dsDNA autoantibodies. Symptoms of rheumatoid arthritis similarly may differ from individual to individual, or temporally or in severity within the same individual. Symptoms may include swollen, warm or tender joints, joint stiffness, fatigue, weight loss, or fever. Pemphigus vulgaris symptoms also may differ from individual to individual, or temporally or in severity within the same individual, and may include painful blisters in the mouth or on the skin, which may appear, disappear, then reappear, and may include peeling, oozing, or crusting of blister sites. Methods of treating these or other diseases or symptoms relating to defective or ineffective GC B-cell tolerance mechanisms by administration of 2OHOA are explicitly included within the present disclosure.

A method of treatment may involve administering 2OHOA to an individual who exhibits a symptom or symptoms that is or is believed to be characteristic of SLE, rheumatoid arthritis, pemphigus vulgaris, or another disease involving autoantibody production, or who has exhibited such symptoms, or who is or is believed to be at risk for exhibiting such symptoms. Treatment may include administering a compound, with the purpose of minimizing, eliminating, preventing, reducing, ameliorating, or controlling such a symptom or symptoms. In some examples, 2OHOA is administered to a human subject, but in other examples, 2OHOA may be administered to a non-human animal subject exhibiting symptoms typical of an animal model of SLE or other autoimmune disorder. For example, 2OHOA may be administered to a mouse exhibiting a model of an autoimmune disease such as of SLE. As an example, 2OHOA may be administered to a mouse of strain NZBWF1, MRLIpr, BXSBYaa, or an animal in a pristane-induced lupus model, or induced chronic graft-versus-host disease model, or other genetic or induced model of SLE or other autoimmune disease. Other examples, such as animal models of rheumatoid arthritis, include conditions where symptoms or indicia resembling rheumatoid arthritis are induced, such as collagen-induced arthritis, collagen-antibody-induced arthritis, zymosan-induced arthritis, and the methylated BSA model, or genetic models such as the TNF-alpha-transgenic mouse, K/BxN mouse, or the Skg mouse. Administration of 2OHOA in such non-human animal models may be used in, for example, screens of other compounds to test their effectiveness or effect on symptoms of autoimmune disorders.

2OHOA may be administered on its own, or in conjunction or together with another compound or compounds which also treat SLE or another autoimmune disease. Such treatment or treatments may include an immunosuppressant compound, a corticosteroid, a non-steroidal anti-inflammatory compound, an anti-malarial compound, an anti-B-cell-specific surface antigen antibody, an anti-B cell activating factor antibody, or any combination of two or more of the foregoing. A second compound administered together with 2OHOA may be administered before 2OHOA is administered, after 2OHOA is administered, or together with 2OHOA. In some examples, a single formulation containing 2OHOA and another or more than one other compound for treatment of an autoimmune disease may be administered. Reference to a "second" compound in addition to 2OHOA does not suggest, absent explicit indication, that 2OHOA needs to be administered before, at the same time as, or after the other compound or compounds and is intended merely to specify that there is more than one compound being or to be administered, irrespective of relative timing of administration thereof.

In some embodiments, a method in accordance with the present disclosure may include contacting a sample with 2OHOA, where the sample includes cells that were removed from a human or other animal subject. For example, a tissue sample may be taken from a human subject with or suspected of having SLE, rheumatoid arthritis, pemphigus vulgaris, or other autoimmune disorder, or a subject constituting an animal model of such disorder, and such tissue sample contacted with 2OHOA. Such tissue sample may include, for example, B cells or antibodies that have been removed from the subject, and in some examples may have been enriched from the sample taken from the subject. In some examples, the sample may include an immortalized cell line. An effect of 2OHOA on such tissue sample may be induced by contacting the sample with 2OHOA and, in some examples, an effectiveness of 2OHOA in inducing a physiological, cellular, or other response of the tissue may be measured. For example, production of autoantibodies or apoptosis or other measures of cell viability or cell death may be observed or measured in such samples and an effect 2OHOA, alone or in combination with other treatments, either of the tissue sample or of the subject from which the sample was taken, on such observations or measurements may be determined.

Formulations for administration to a subject include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of a recipient or intended purpose of the administration. A formulation may conveniently be presented in unit dosage form and may be prepared by any of the methods well known in the art of pharmacy. Methods may include a step of bringing into association 2OHOA or a pharmaceutically acceptable salt thereof ("active ingredient") with a carrier which constitutes one or more accessory ingredients. In general, formulations may be prepared by uniformly and intimately bringing into association an active ingredient with liquid carriers or finely divided solid carriers or both and then, if necessary, shaping the product into the desired formulation.

Formulations of the present disclosure suitable for oral administration may be presented as discrete units such as capsules, cachets or tablets each containing a predetermined amount of an active ingredient; as a powder or granules; as a solution or a suspension in an aqueous liquid or a non-aqueous liquid; or as an oil-in-water liquid emulsion or a water-in-oil liquid emulsion. 2OHOA may also be presented as a bolus, electuary or paste. For oral or other administration, 2OHOA may be suspended in a solution, or dissolved in a solvent, such as alcohol, DMSO, water, saline, or other solvent, which may be further diluted or dissolved in another solution or solvent, and may or may contain a carrier or other excipient in some examples.

In certain embodiments, 2OHOA may be incorporated with excipients and used in the form of ingestible tablets, buccal tablets, troches, capsules, elixirs, suspensions, syrups, wafers, and the like. Tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

A tablet may be made by compression or molding, optionally with one or more accessory ingredients. Compressed tablets may be prepared by compressing in a suitable machine an active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. Tablets may optionally be coated or scored and may be formulated so as to provide sustained, delayed or controlled release of an active ingredient therein.

Formulations for parenteral or other administration include aqueous and non-aqueous sterile injection solutions which may contain anti-oxidants, buffers, bacteriostats and solutes which render a formulation isotonic with the blood of the intended recipient. Formulations for parenteral or other administration also may include aqueous and non-aqueous sterile suspensions, which may include suspending agents and thickening agents. The formulations may be presented in unit-dose of multi-dose containers, for example sealed ampoules and vials, and may be stored in a freeze-dried (lyophilized) condition requiring only the addition of a sterile liquid carrier, for example saline, phosphate-buffered saline (PBS) S) or the like, immediately prior to use. Extemporaneous injection solutions and suspensions may be prepared from sterile powders, granules and tablets of the kind previously described.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of 2OHOA to polymer and the nature of the particular polymer employed, the rate of 2OHOA release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose.

A 2OHOA formulation may include different types of carriers depending on whether it is to be administered in solid, liquid or aerosol form, and whether it needs to be sterile for such routes of administration as injection. The present invention can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990.

The term "pharmaceutically acceptable salt" refers to salts prepared from pharmaceutically acceptable non-toxic acids or bases including inorganic acids and bases and organic acids and bases. When the compounds of the present invention are basic, salts may be prepared from pharmaceutically acceptable non-toxic acids including inorganic and organic acids. Suitable pharmaceutically acceptable acid addition salts for the compounds of the present invention include acetic, adipic, alginic, ascorbic, aspartic, benzenesulfonic (besylate), benzoic, betulinic, boric, butyric, camphoric, camphorsulfonic, carbonic, citric, ethanedisulfonic, ethanesulfonic, ethylenediaminetetraacetic, formic, fumaric, glucoheptonic, gluconic, glutamic, hydrobromic, hydrochloric, hydroiodic, hydroxynaphthoic, isethionic, lactic, lactobionic, laurylsulfonic, maleic, malic, mandelic, methanesulfonic, mucic, naphthylenesulfonic, nitric, oleic, pamoic, pantothenic, phosphoric, pivalic, polygalacturonic, salicylic, stearic, succinic, sulfuric, tannic, tartaric acid, teoclatic, p-toluenesulfonic, ursolic and the like. When the compounds contain an acidic side chain, suitable pharmaceutically acceptable base addition salts for the compounds of the present invention include, but are not limited to, metallic salts made from aluminum, calcium, lithium, magnesium, potassium, sodium and zinc or organic salts made from lysine, arginine, N,N'-dibenzylethylenediamine, chloroprocaine, choline, diethanolamine, ethylenediamine, meglumine (N-methylglucamine) and procaine. Further pharmaceutically acceptable salts include, when appropriate, nontoxic ammonium cations and carboxylate, sulfonate and phosphonate anions attached to alkyl having from 1 to 20 carbon atoms.

2OHOA may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

As used herein, the term "physiologically functional derivative" refers to any pharmaceutically acceptable derivative of a compound of the present invention that, upon administration to a mammal, is capable of providing (directly or indirectly) a compound of the present invention or an active metabolite thereof. Such derivatives, for example, esters and amides, will be clear to those skilled in the art, without undue experimentation. Reference may be made to the teaching of Burger's Medicinal Chemistry And Drug Discovery, 5 th Edition, Vol 1: Principles and Practice.

As used herein, the term "effective amount" means an amount of 2OHOA pharmaceutical agent that may elicit a biological or medical response of a cell, tissue, system, animal, or human that is being sought, for instance, by a researcher or clinician. The term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function. For use in therapy, therapeutically effective amounts of 2OHOA, as well as salts, solvates, and physiological functional derivatives thereof, may be administered as the raw chemical. Additionally, the active ingredient may be presented as a pharmaceutical composition.

Pharmaceutical compositions of the present invention include an effective amount of 2OHOA and optionally one or more additional agents dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains 2OHOA and optionally one or more additional active ingredient will be known to those of skill in the art in light of the present disclosure, as exemplified by Remington's Pharmaceutical Sciences, 18th Ed. Mack Printing Company, 1990. Moreover, for animal (e.g., human) administration, it will be understood that preparations should meet sterility, pyrogenicity, general safety and purity standards as required by FDA Office of Biological Standards.

Further in accordance with the present invention, the composition of the present invention suitable for administration may be provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of the composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, 2OHOA may be combined with a carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of pharmaceutical lipid vehicle compositions that include 2OHOA, and may also include an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, 2OHOA may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to a subject (e.g., an animal or human patient) can be determined by physical and physiological factors such as body weight, severity of condition, the type of disease being treated, previous or concurrent therapeutic interventions, idiopathy of the patient and on the route of administration, and purpose of treatment. Depending upon the dosage and the route of administration, the number of administrations of a preferred dosage and/or an effective amount may vary according to the response of the subject or purpose of treatment. The practitioner responsible for administration will, in any event, determine the concentration of active ingredient(s) in a composition and appropriate dose(s) for the individual subject.

In certain embodiments, pharmaceutical compositions may include, for example, at least about 0.1% of an active compound. In other embodiments, an active compound may comprise between about 2% to about 75% of the weight of the unit, or between about 25% to about 60%, for example, and any range derivable therein. Naturally, the amount of 2OHOA in each therapeutically useful composition may be prepared in such a way that a suitable dosage will be obtained in any given unit dose of the compound. Factors such as solubility, bioavailability, biological half-life, route of administration, product shelf life, as well as other pharmacological considerations will be contemplated by one of ordinary skill in the art of preparing such pharmaceutical formulations, and as such, a variety of dosages and treatment regimens may be desirable.

In other non-limiting examples, a dose may also comprise from about 1 microgram/kg body weight, about 5 microgram/kg body weight, about 10 microgram/kg body weight, about 50 microgram/kg/body weight, about 100 microgram/kg body weight, about 200 microgram/kg body weight, about 350 microgram/kg body weight, about 500 microgram/kg body weight, about 1 milligram/kg body weight, about 5 milligram/kg body weight, about 10 milligram/kg body weight, about 50 milligram/kg body weight, about 100 milligram/kg body weight, about 200 milligram/kg body weight, about 350 milligram/kg body weight, about 500 milligram/kg body weight, to about 1000 mg/kg body weight or more per administration, and any range derivable therein. In non-limiting examples of a derivable range from the numbers listed herein, a range of about 5 mg/kg body weight to about 100 mg/kg body weight, about 5 microgram/kg/body weight to about 500 milligram/kg body weight, etc., can be administered, based on the numbers described above.

Dosing can be modified or chosen based on factors including purpose of treatment, severity of symptoms, or an individual subject's body mass. A daily dose may be administered once per day, or distributed over 2, 3, 4, 5, 6, 7, 8, or more administrations per day. A daily dose me be between 10 mg and 20 g per day. A daily dose may be less than 10 mg, for example 5 mg or 1 mg per day, or in a range of between 1-5 mg or between 5-10 mg. A daily dose may be between 10 mg and 50 mg, or between 50 mg and 100 mg, or between 100 mg and 150 mg, or between 150 mg and 200 mg, or between 200 mg and 250 mg, or between 250 mg and 300 mg, or between 300 mg and 350 mg or between 350 m and 400 mg or between 400 mg and 450 mg or between 450 mg and 500 mg. A daily dose may be between 500 mg and 600 mg, or between 600 mg and 700 mg, or between 700 mg and 800 mg, or between 900 mg and 1 g, or between 1 g and 1500 mg, or between 1500 mg and 2 g, or between 2 g and 2500 mg, or between 2500 mg and 3 g, or between 3 g and 3500 mg, or between 3500 mg and 4 g, or between 4 g and 4500 mg, or between 4500 mg and 5 g. A daily dose may be between 5 g and 6 g, or between 6 g and 7 g, or between 7 g and 8 g, or between 8 g and 9 g, or between 9 g and 10 g, or between 10 g and 11 g, or between 11 g and 12 g, or between 12 and 13 g, or between 13 g and 14 g, or between 14 g and 15 g, or between 15 g and 16 g, or between 16 g and 17 g, or between 17 g and 18 g, or between 18 g and 19 g, or between 19 g and 20 g. Al subranges within and between any of these ranges are also included within the present disclosure.

In some embodiments, 2OHOA may be formulated to be administered via an alimentary route. Alimentary routes include all possible routes of administration in which the composition is in direct contact with the alimentary tract. Specifically, 2OHOA may be administered orally, buccally, rectally, or sublingually. As such, 2OHOA may be formulated with an inert diluent or with an assimilable edible carrier, or may be enclosed in hard- or soft-shell gelatin capsule, or may be compressed into tablets, or may be incorporated directly with the food of the diet.

For oral administration 2OHOA may alternatively be incorporated with one or more excipients in the form of a mouthwash, dentifrice, buccal tablet, oral spray, or sublingual orally-administered formulation. For example, a mouthwash may be prepared incorporating 2OHOA in the required amount in an appropriate solvent, such as a sodium borate solution (Dobell's Solution). Alternatively, 2OHOA may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively 2OHOA may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

In further embodiments, the 2OHOA may be administered via a parenteral route. As used herein, the term "parenteral"

includes routes that bypass the alimentary tract. Specifically, 2OHOA may be administered for example, but not limited to intravenously, intradermally, intramuscularly, intraarterially, intrathecally, subcutaneous, or intraperitoneally.

Solutions of 2OHOA as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions. In all cases the form may be sterile and fluid to the extent that easy injectability exists. A carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution may be suitably buffered if necessary and a liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations may meet sterility, pyrogenicity, general safety and purity standards as required by FDA Office of Biologics standards.

Sterile injectable solutions may be prepared by incorporating 2OHOA in the required amount in the appropriate solvent with various of the other ingredients enumerated above, as required, followed by filtered sterilization. Generally, dispersions may be prepared by incorporating various sterilized active ingredients into a sterile vehicle which contains the basic dispersion medium and the required other ingredients from those enumerated above. In the case of sterile powders for the preparation of sterile injectable solutions, preferred methods of preparation include vacuum-drying and freeze-drying techniques which yield a powder of the active ingredient plus any additional desired ingredient from a previously sterile-filtered solution thereof. A powdered composition may be combined with a liquid carrier such as, e.g., water or a saline solution, with or without a stabilizing agent.

In other embodiments 2OHOA may be formulated for administration via various miscellaneous routes, for example, topical (i.e., transdermal) administration, mucosal administration (intranasal, vaginal, etc.) and/or inhalation.

Pharmaceutical compositions for topical administration may include 2OHOA formulated for a medicated application such as an ointment, paste, cream or powder. Ointments include all oleaginous, adsorption, emulsion and water-solubly based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described. Likewise, the delivery of drugs using intranasal microparticle resins and lysophosphatidyl-glycerol compounds are also well-known in the pharmaceutical arts. Likewise, transmucosal drug delivery in the form of a polytetrafluoroetheylene support matrix may be adopted for use in accordance with the present disclosure.

The term aerosol refers to a colloidal system of finely divided solid of liquid particles dispersed in a liquefied or pressurized gas propellant. An aerosol of the present invention for inhalation may consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

In a further embodiment, disclosed herein is an animal model for evaluating the ability of potential therapeutic agents for the treatment of SLE or other autoimmune disorders, such as autoimmune disorders characterized by maladaptive B cell tolerance. Examples may include SLE, rheumatoid arthritis, and pemphigus vulgaris. In an embodiment, an animal may have reduced SMS2 expression or activity, resulting in the exhibition of one or more cellular, physiological, or other indicia of autoimmune pathology, and a treatment may be administered to such animal and tested for its ability to ameliorate, reverse, prevent, minimize, or reduce one or more pathological indicia. For example, $Sgms2^{-/-}$ mice may be used in such a model. $Sgms2^{-/-}$ mice may be engineered by methods such as replacing the sequence of the Sgms2 gene coding for the translational start signal for SMS2 synthesis with a sequence that does not code for such a translational start signal, resulting in lack of SMS2 production from any mRNA transcribed from such a modified gene. Other modifications to the Sgms2 gene resulting in low or no SMS2 expression may similarly be used. In other examples, SMS2 expression may be reduced by other known methods, such as antisense RNA technology, aptamers, siRNA or other methods of interfering with or reducing translation of SMS2 protein from its mRNA. The known sequence and chromosomal locus of the Sgms2 gene may be used by skilled artisans to reduce or eliminate SMS2 production by such methods, as would be understood by skilled artisans on the basis of the present disclosure. Yuyama et al., (2012) Sphingolipid-modulated exosome secretion promotes clearance of amyloid-β by microglia, J Biol Chem. 28710977-89.

In other examples, activity of SMS2 protein may be disrupted. For example, a portion or portions of the sequence of the Sgms2 gene corresponding to one or more amino acid sequence of the SMS2 protein important or essential for its activity may be modified such that SMS2 protein produced as a result of expression of such modified gene is incapable of performing its functions as disclosed herein. In other examples, SMS2 activity may be inhibited by contacting SMS2 with a compound that disrupts its activity. Examples of such compounds are known to skilled artisans. Adachi et al. (2017) Discovery and characterization of selective human sphingomyelin synthase 2 inhibitors, European Journal of Medicinal Chemistry 136:283-293.

In some examples, indicia of autoimmune-related disorders or pathologies measured in an animal model as disclosed herein may include increased serum ANA, proteinuria, glomerulonephritis, kidney immune complex, reduced or defective apoptosis in B cells, or other such indicia. In still further examples, a treatment or compound that is believed, theorized, expected, predicted, or otherwise considered for testing for its ability to be a treatment for an autoimmune disorder may be administered to an animal model with reduced SMS2 expression and/or activity, such as disclosed above, and the treatment or compound tested for its ability to ameliorate, reverse, prevent, minimize, or reduce one or more pathological indicia or symptoms of SLE, rheumatoid arthritis, and pemphigus vulgaris, or other autoimmune disorder, such as any one or more of the foregoing indicia.

EXAMPLES

The following examples are presented to further describe techniques in accordance with the method disclosed herein, but should not be read as limiting, because variations still within the scope of embodiments of the present invention will be apparent to those skilled in the art.

Sphingomyelin synthase 2 (SMS2), an enzyme producing sphingomyelin (SM) and diacylglycerol (DAG) on the plasma membrane, is critical for enforcing B cell tolerance via activation of PKCδ-mediated apoptosis in GC B cells. As disclosed herein, Sgms2$^{-/-}$ mice had a lupus-like disease associated with increased numbers of anti-dsDNA GC B cells due to an intrinsic defect in B cell apoptosis. Nuclear translocation of PKCδ, a DAG-activated kinase required for the prevention of SLE pathogenesis, was diminished in Sgms2$^{-/-}$ GC B cells. Upregulation of SMS2 activity promoted PKCδ's pro-apoptotic activity in B cells, and inhibited anti-dsDNA IgG production in NZBWF1 mice, a spontaneous SLE mouse model without any known alterations in Sgms2 or Prkcd, suggesting that the SMS2/PKCδ signaling pathway could be targeted to restore peripheral B cell tolerance in SLE.

Sgms2$^{-/-}$ mice were originally made by homologous recombination-mediated disruption of exon 2 in Sgms2 on a 129 background, and then backcrossed to C57/BL6 strain for 4 generations for studying the role of SMS2 in atherosclerosis in Dr. Xian-cheng Jiang's lab. These mice were further backcrossed to C57BL/6 strain for 4-5 generations to generate≥93.6% pure C57BL/6 background (Jackson Lab's genome scan) for autoimmune study in our lab. Sgms2$^{-/-}$ mice are born at a normal Mendelian frequency and appear to develop normally. Routine flow cytometry analysis showed that lymphocyte development in the bone marrow to be normal in Sgms2$^{-/-}$ mice, although analysis of peripheral blood and splenic lymphocytes did not detect significant abnormalities in young adults (8-15 week old). Strikingly, in 20-24 week old Sgms2$^{-/-}$ mice, coincident with slightly increased total IgG, significantly increased anti-dsDNA IgG titers in blood was detected by Elisa and anti-nuclear antigen (ANA) substrate slide tests, signifying a SLE pathogenesis. FIG. 1A, left panel, shows serum anti-nuclear antibodies (ANA) in Sgms2$^{-/-}$ mice. Hep2 cell substrate slides were incubated with sera harvested from 5-6-month-old Sgms2$^{-/-}$ and Sgms2$^{+/+}$ littermates (i.e., the Sgms2$^{+/+}$ littermates have wild-type Sgms2 gene and unadulterated SMS2 expression). Nuclear antigens bound IgGs were detected by FITC-conjugated anti-mouse IgG antibody (green). Serum from mice of the MRL-lpr strain, a mouse model of SLE, was used as a positive control. FIG. 1A, right panel, shows serum titers of anti-dsDNA antibodies in Sgms2$^{-/-}$ mice. Serum samples were harvested from 9 pairs of Sgms2$^{-/-}$ and Sgms2$^{+/+}$ littermates, and 7 pairs of Sgms1$^{-/-}$ and Sgms1$^{+/+}$ littermates. Concentrations of anti-dsDNA IgGs were measured by ELISA.

Figure 1B:
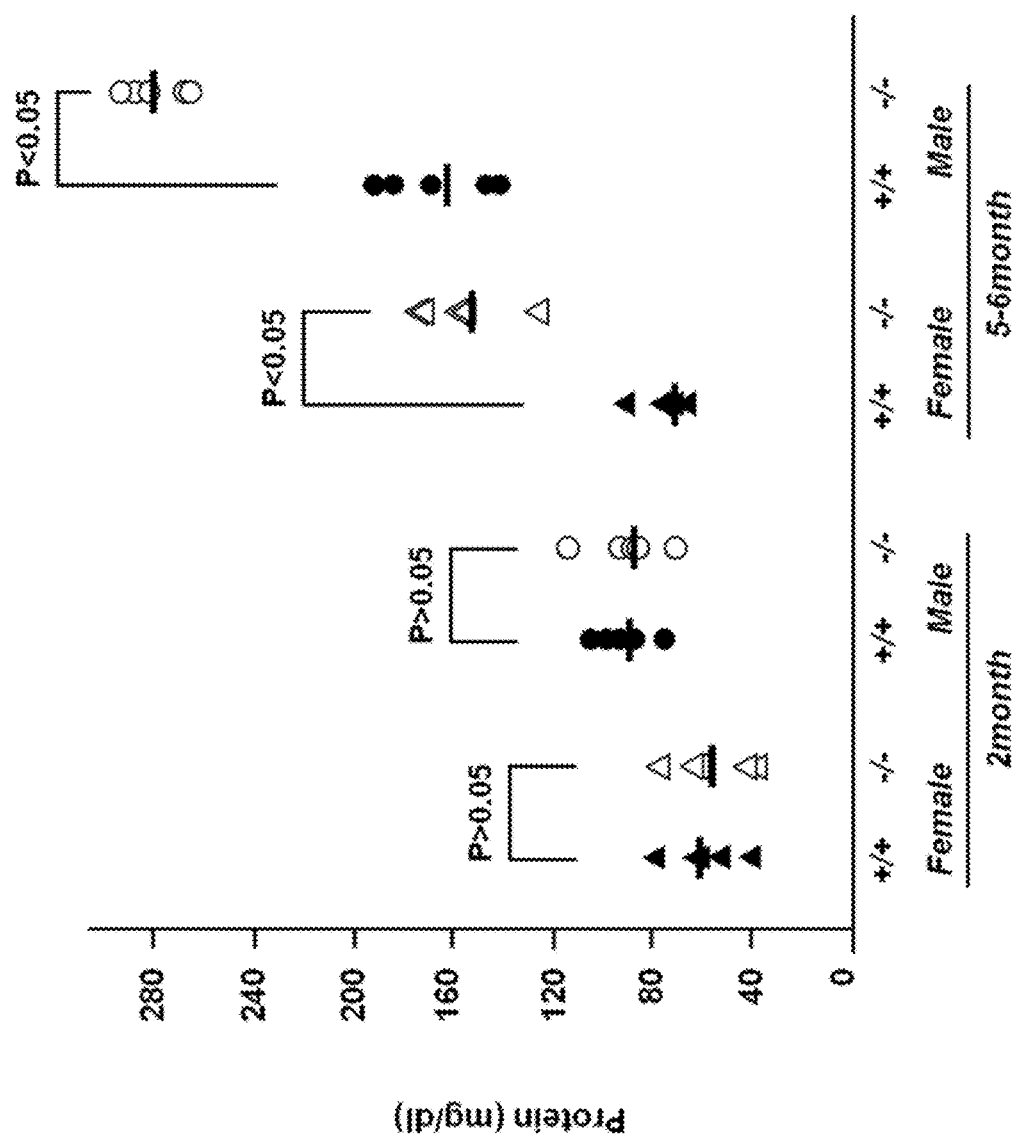
FIG. 1B shows graphical evidence of proteinuria in Sgms2$^{-/-}$ mice.
Figure 1C:
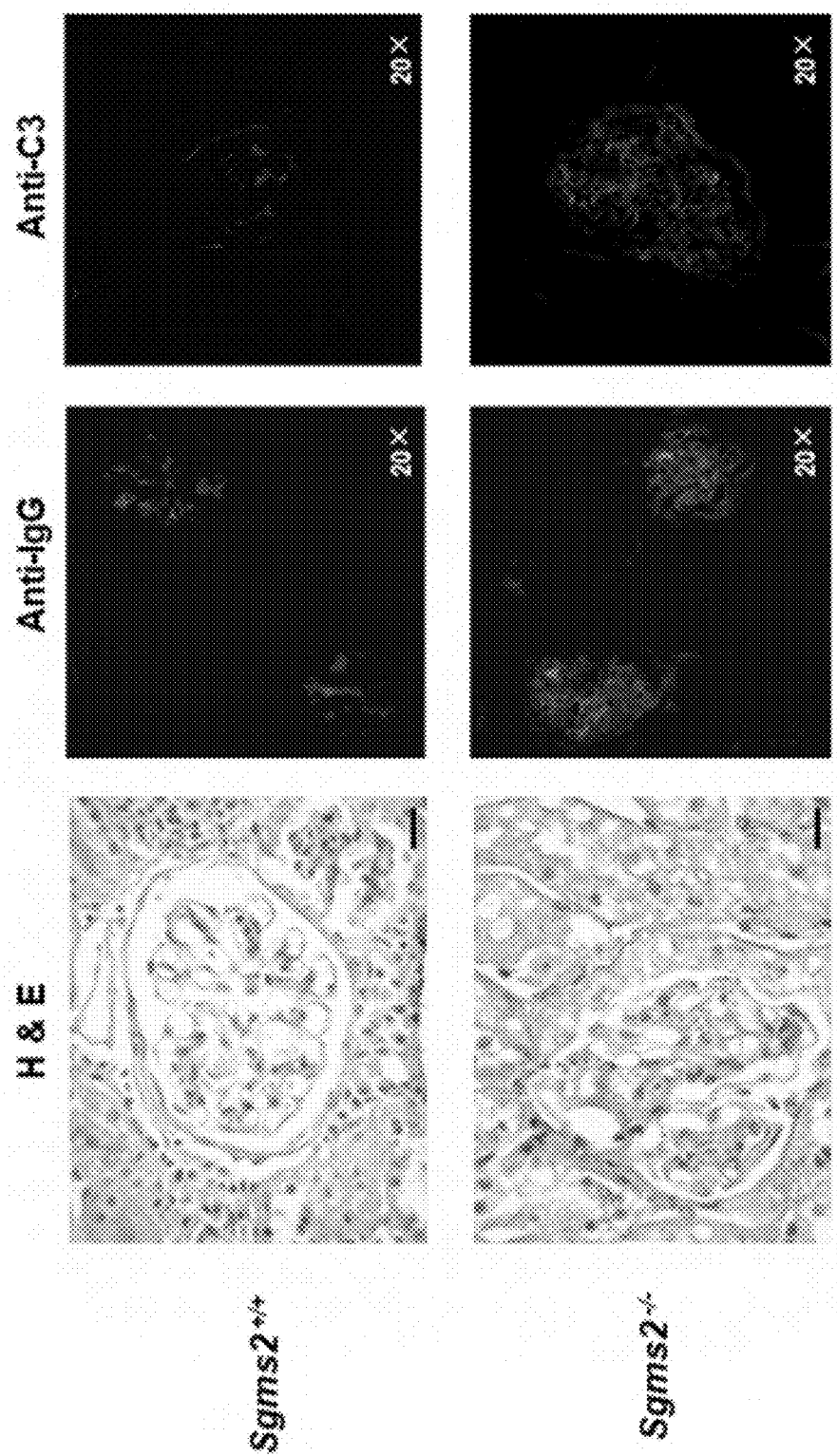
FIG. 1C shows photomicrographic evidence of glomerulonephritis and kidney immune complex in Sgms2$^{-/-}$ mice.

Indeed these Sgms2$^{-/-}$ mice had proteinuria and glomerulonephritis similar to renal pathology observed in SLE patients. FIG. 1B shows proteinuria in Sgms2$^{-/-}$ mice. Urine was collected from Sgms2$^{-/-}$ and Sgms2$^{+/+}$ mice at the indicated age. Protein concentration was measured by a standard Bradford protein assay. Each symbol represents one mouse. FIG. 1C shows glomerulonephritis and kidney immune complex in Sgms2$^{-/-}$ mice. Shown are H&E staining of (left), and immunofluorescent anti-mouse IgG (middle) and anti-complement C3 protein (right) staining of Sgms2$^{-/-}$ and Sgms2$^{+/+}$ kidney sections. Results are representative of 3 independent experiments. Immunofluorescent staining confirmed the deposition of IgGs and complement component 3 protein in glomeruli (FIG. 1C). In contrast, genetic deficiency of SMS1, the other major SMS isoform in mammalian cells that carries out the identical reaction as SMS2, except on the Golgi membrane, did not cause these abnormalities, (FIG. 1A), suggesting that SMS2 activity on the plasma membrane has a non-redundant role in protecting against SLE-like disease.

Figure 2A:
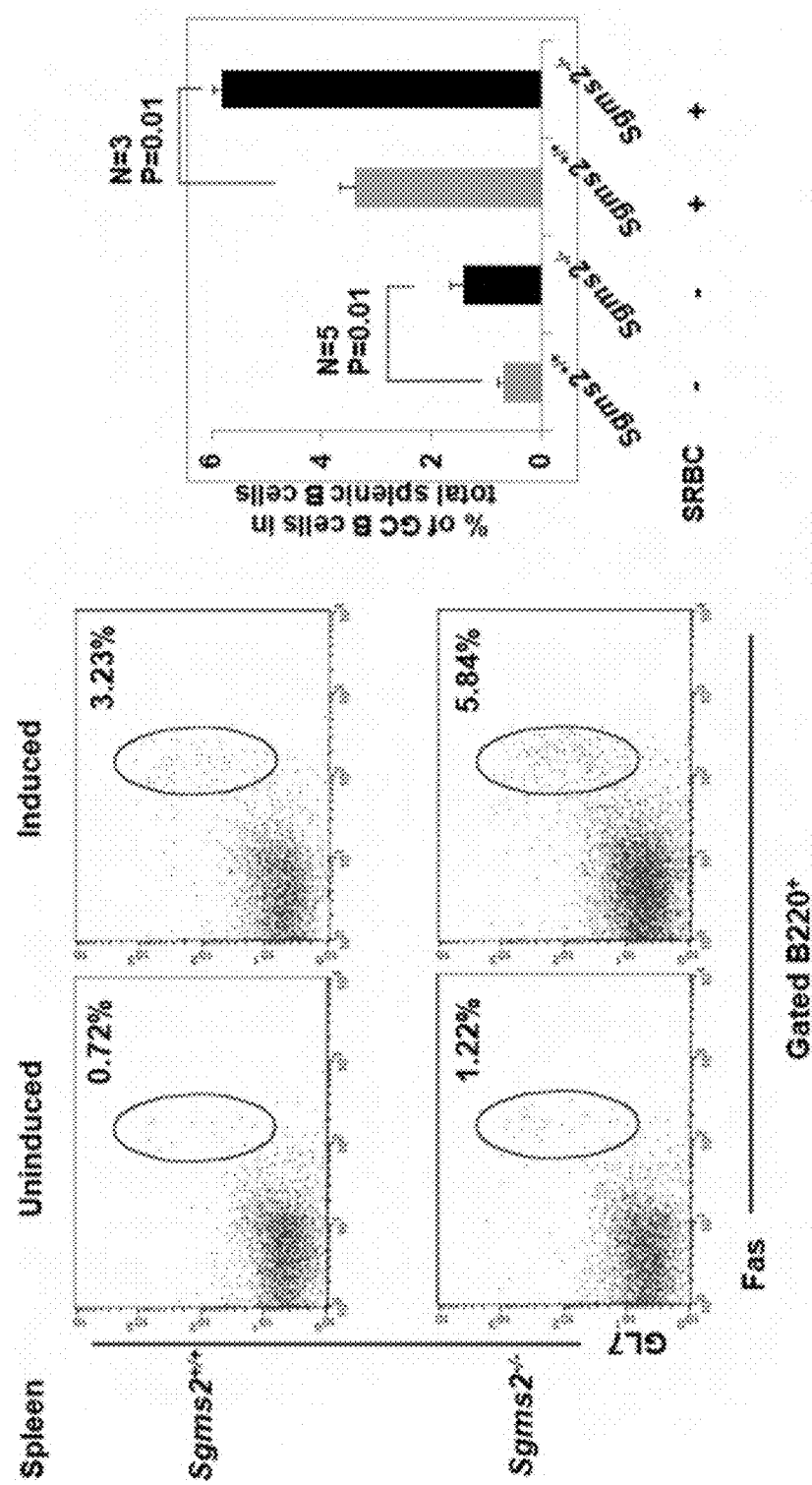
FIG. 2A shows scatterplot (left panel) and graphical (right panel) evidence from flow cytometry analysis of increased splenic germinal center (GC) B cells in Sgms2$^{-/-}$ mice.
Figure 2B:
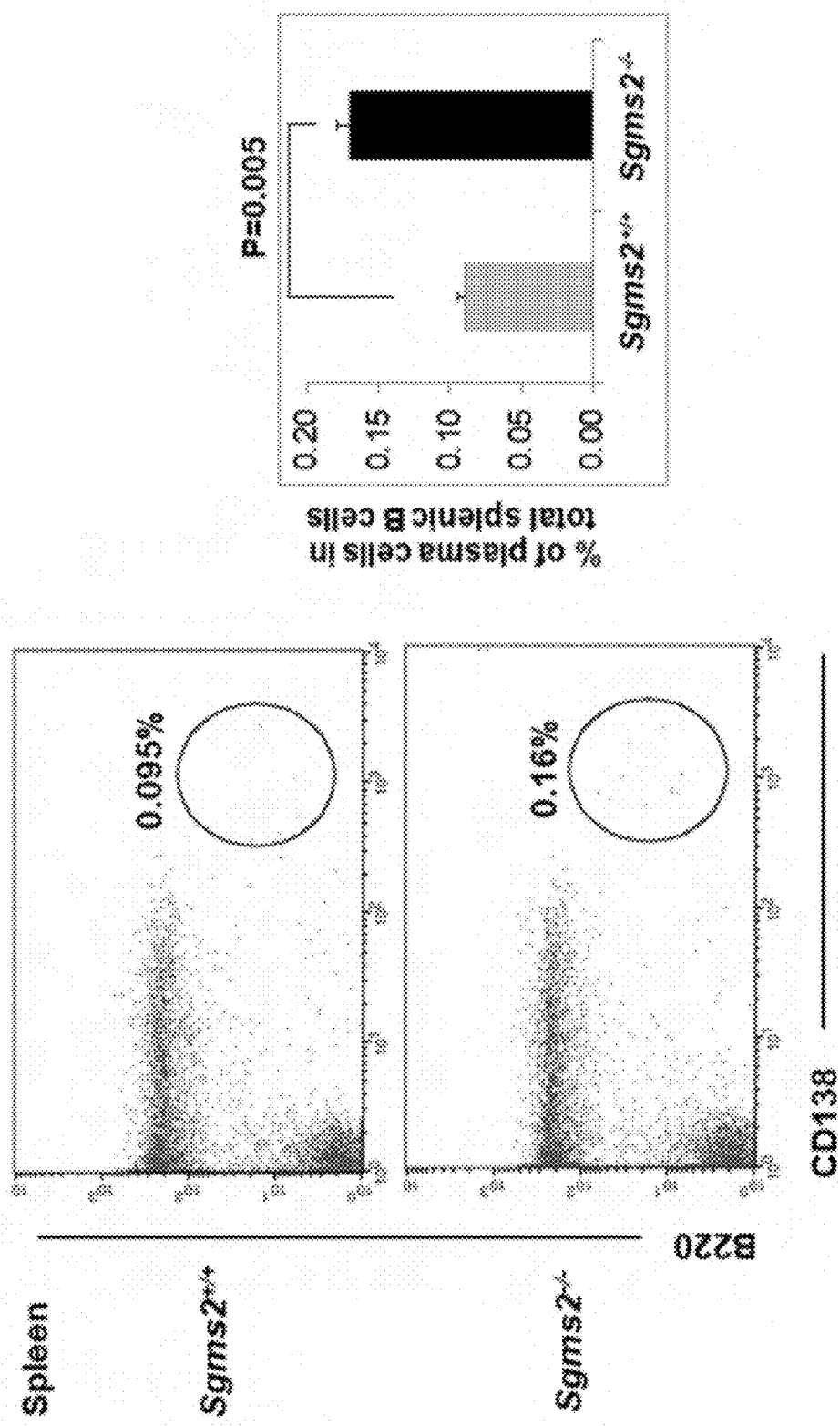
FIG. 2B shows scatterplot (left panel) and graphical (right panel) evidence from flow cytometry analysis of increased plasma cells in Sgms2$^{-/-}$ mice.

A more detailed analysis of splenic B cell subsets shows that Sgms2$^{-/-}$ mice had significantly increased GC B cells and plasma cells in the spleens of Sgms2$^{-/-}$ mice. FIG. 2A shows increased splenic GC B cells in Sgms2$^{-/-}$ mice. Splenic cells were collected from Sgms2$^{-/-}$ and Sgms2$^{+/+}$ littermates with or without GC induction by IP injections of sheep red blood cells (SRBCs). Percentages of GL-7$^+$Fas$^+$ GC B cells in total splenic B cells were analyzed by flow cytometry. Statistical data are generated from 3 pairs of SRBC treated and 5 pairs of untreated Sgms2$^{-/-}$ and Sgms2$^{+/+}$ littermates. Student's t-test was used in the analysis. FIG. 2B shows increased plasma cells in Sgms2$^{-/-}$ mice. Percentages of B220$^+$CD138$^+$ plasma cells in total splenic cells were analyzed by flow cytometry. Statistical data were generated from 4 pairs of Sgms2$^{-/-}$ and Sgms2$^{+/+}$ littermates. Student's t-test was used in the analysis.

Figure 2C:
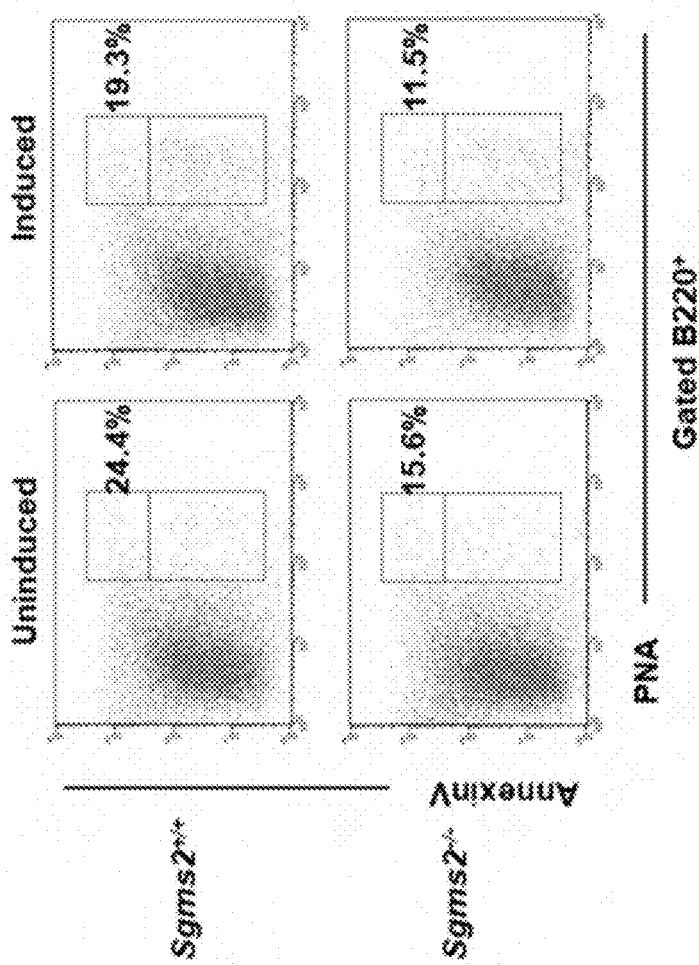
FIG. 2C shows scatterplot (left panel) and graphical (right panel) evidence of reduced apoptosis in Sgms2$^{-/-}$ GC B cells.
Figure 2C:
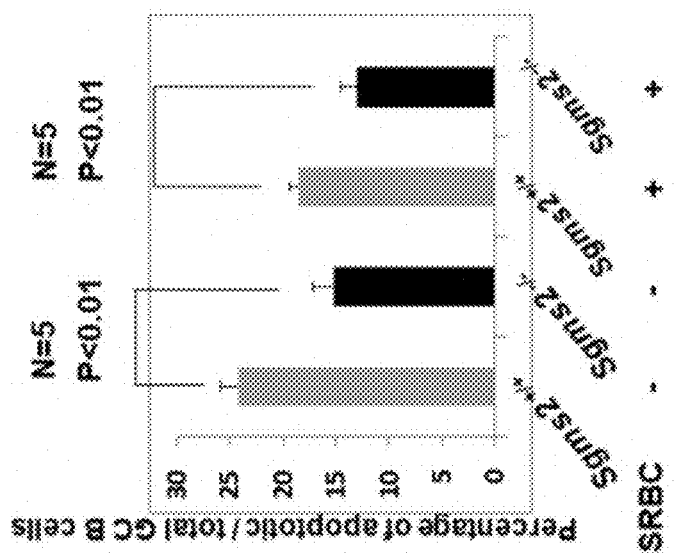
Figure 2D:
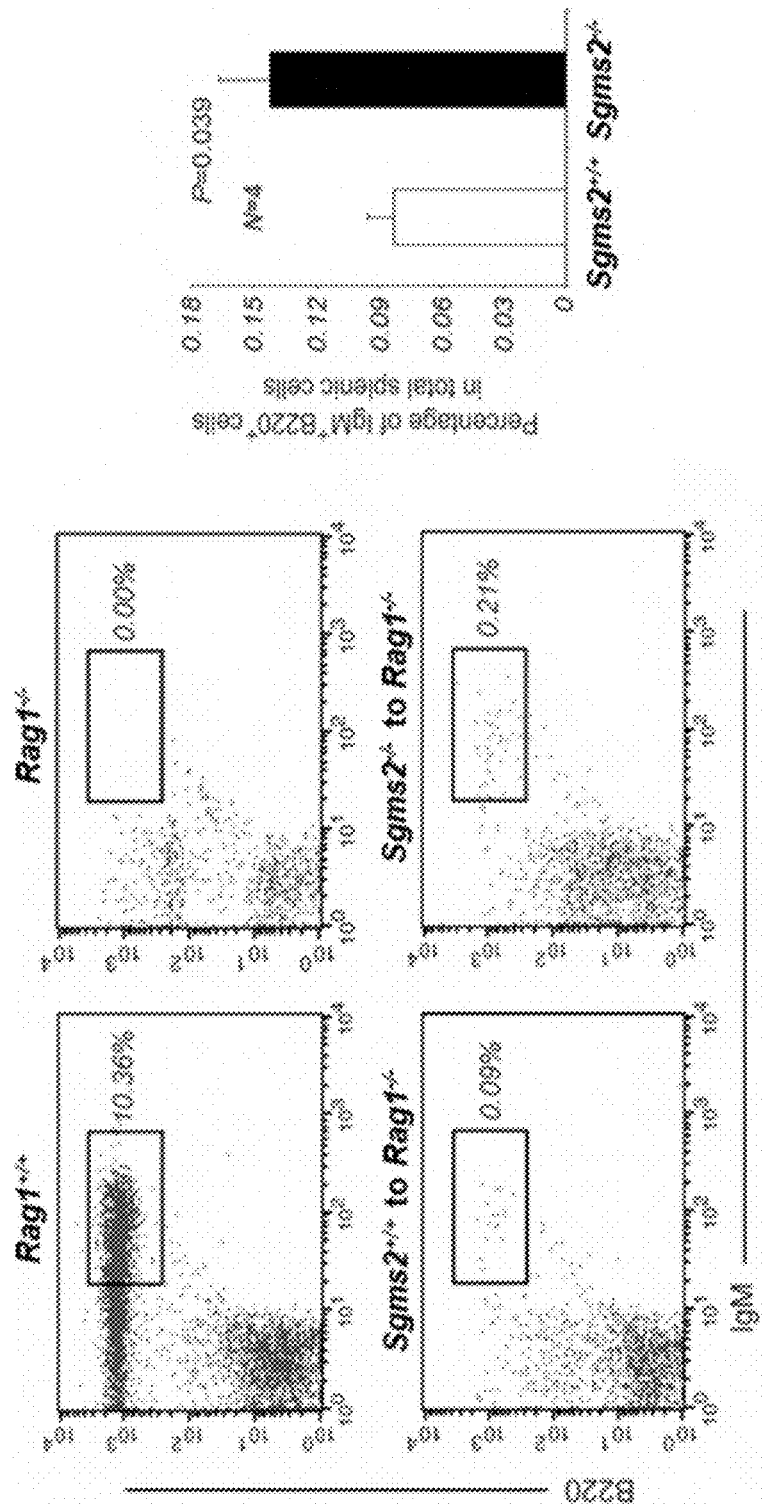
FIG. 2D shows scatterplot (left panel) and graphical (right panel) evidence of intrinsic defective apoptosis in Sgms2$^{-/-}$ B cells.

Moreover, compared to Sgms2$^{+/+}$ GC B cells, Sgms2$^{-/-}$ GC B cells expressed less of the apoptosis marker annexin 5. Shown in FIG. 2C is reduced apoptosis in Sgms2$^{-/-}$ GC B cells. Splenic cells isolated from Sgms2$^{-/-}$ and Sgms2$^{+/+}$ mice with or without GC induction were stained for Annexin V and PNA (left). Percentages of apoptotic GC B cells (B220$^+$ Annexin V$^+$PNA$^+$) in total GC B cells (B220$^+$ PNA$^+$) were indicated. Data represent 5 pairs of Sgms2$^{-/-}$ and Sgms2$^{+/+}$ littermates. The impaired apoptosis in Sgms2$^{-/-}$ GC B cells was likely B cell intrinsic, because mature Sgms2$^{-/-}$ B cells had a much longer lifespan than Sgms2$^{+/+}$ B cells after transplantation into lymphocyte deficient Rag1$^{-/-}$ mice. As shown in FIG. 2D, which shows intrinsic defective apoptosis in Sgms2$^{-/-}$ B cells. Splenic B cells harvested from Sgms2$^{-/-}$ and Sgms2$^{+/+}$ littermates were IV injected into Rag1$^{-/-}$ mice that are deficient of mature lymphocytes. 15 days after the transfer, surviving splenic B cells in Rag1$^{-/-}$ mice were analyzed by flow cytometry.

Figure 2E:
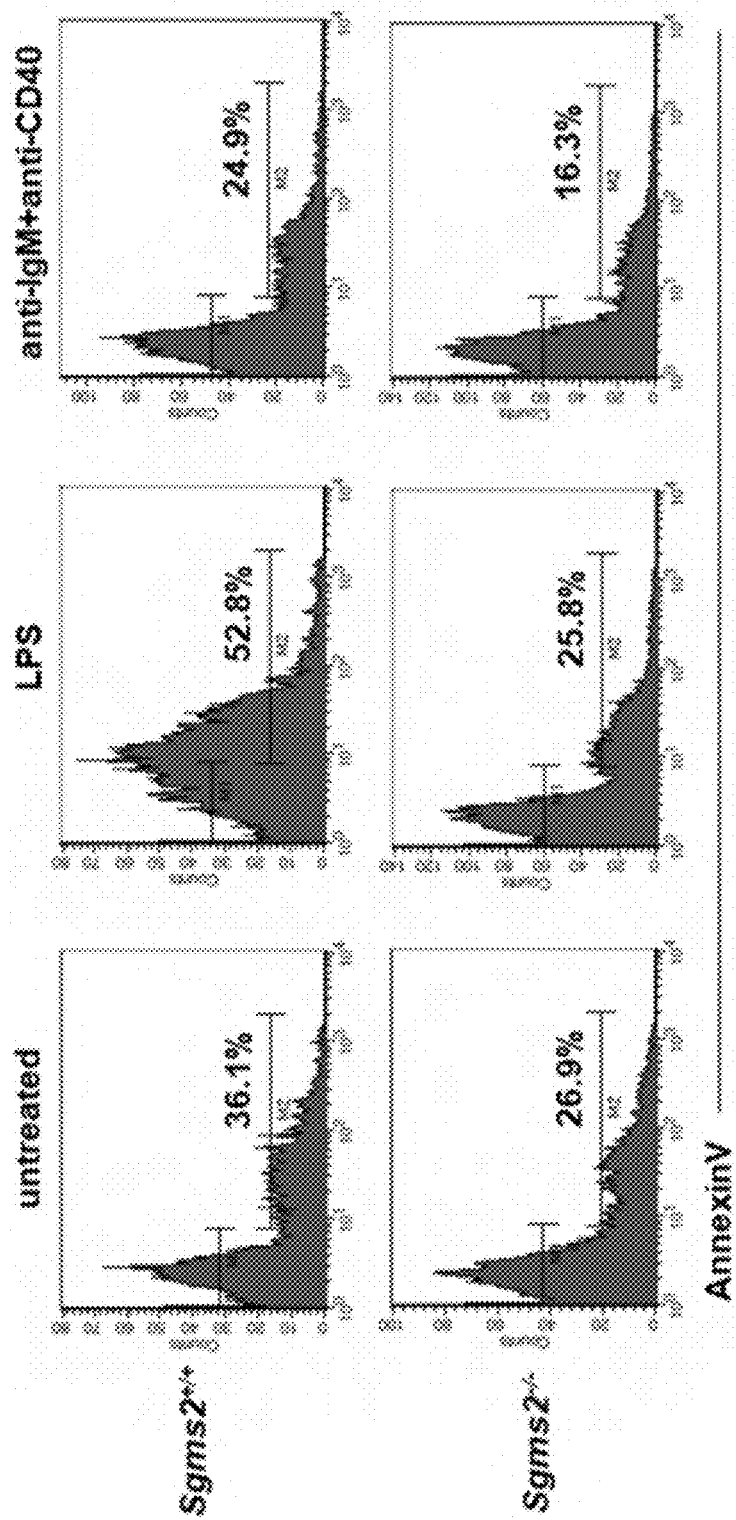
FIG. 2E shows graphical evidence of attenuated apoptosis in cultured Sgms2$^{-/-}$ splenic B cells.
Figure 2F:
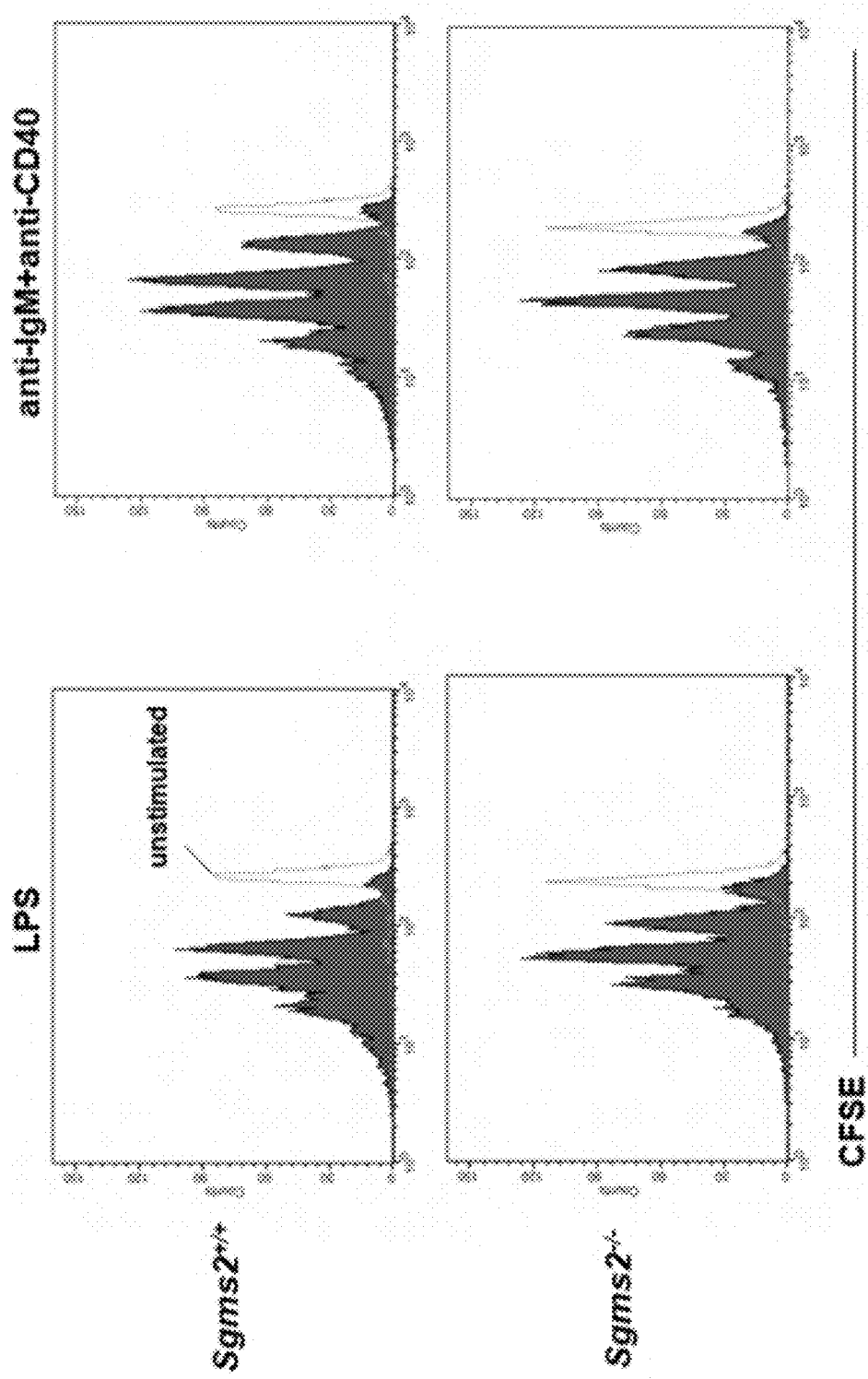
FIG. 2F shows graphical evidence of unaffected proliferation in cultured Sgms2$^{-/-}$ splenic B cells.

Consistent with this, SMS2 deficiency reduced apoptosis but had no effects on the proliferation of B cells in response to BCR stimulation. FIG. 2E, shows attenuated apoptosis in cultured Sgms2$^{-/-}$ splenic B cells. Isolated splenic B cells were cultured for 24 hours in the absence (left) and presence (middle and right) of BCR stimuli, and then stained by anti-Annexin V antibody for flow cytometry analysis of apoptosis. Percentages of Annexin apoptotic cells in total B cells were indicated. Data are representative of three independent experiments. Shown in FIG. 2F is unaffected proliferation in cultured Sgms2$^{-/-}$ splenic B cells. Isolated splenic B cells were labeled with CFSE and cultured for 96 hours in the absence (green curve) and presence (purple filled) of BCR stimuli before the proliferation analysis by flow cytometry.

Figure 2G:
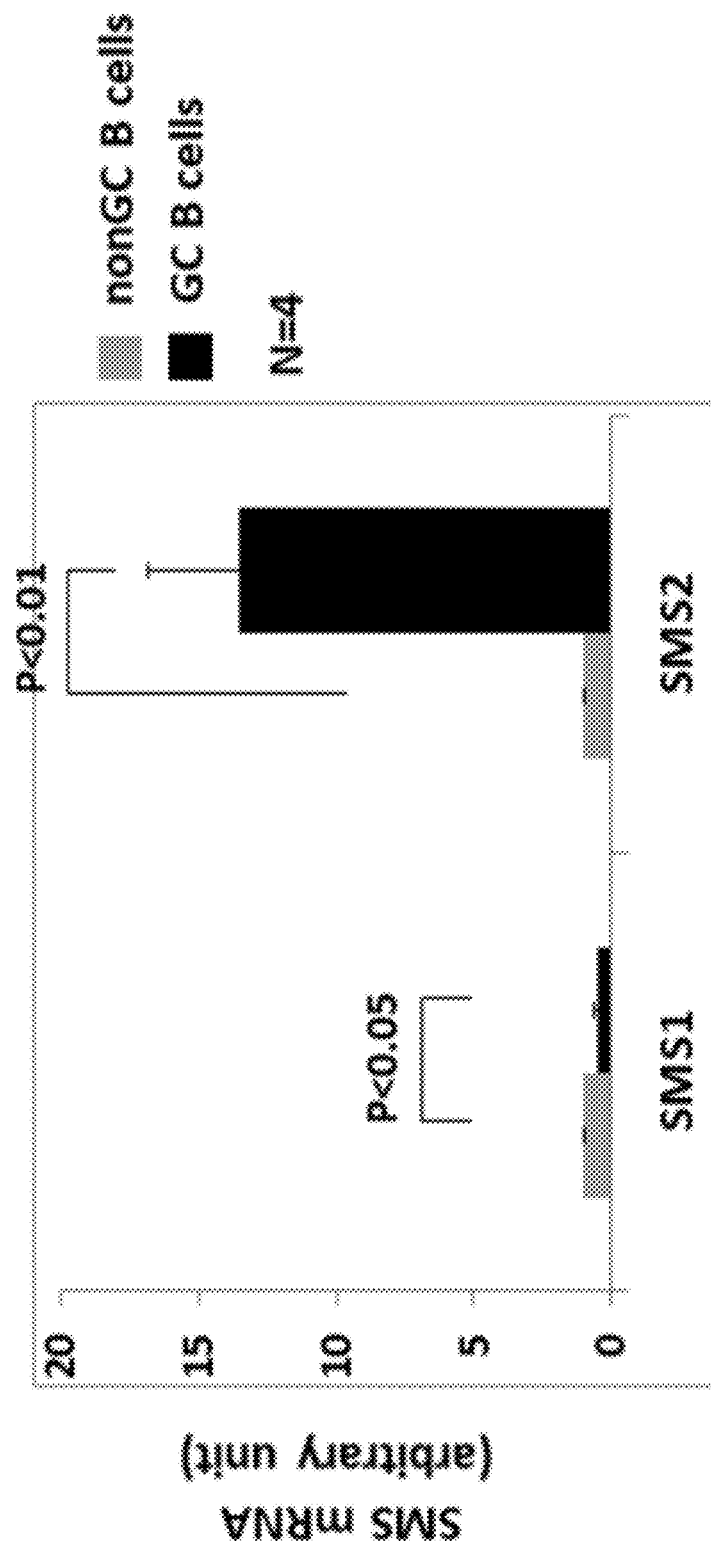
FIG. 2G shows graphical evidence of SMS1 and SMS2 mRNA levels in GC B cells and non-GC B cells isolated from Sgms2$^{+/+}$ mice injected with sheep red blood cells by RT-PCR analysis.
Figure 2H:
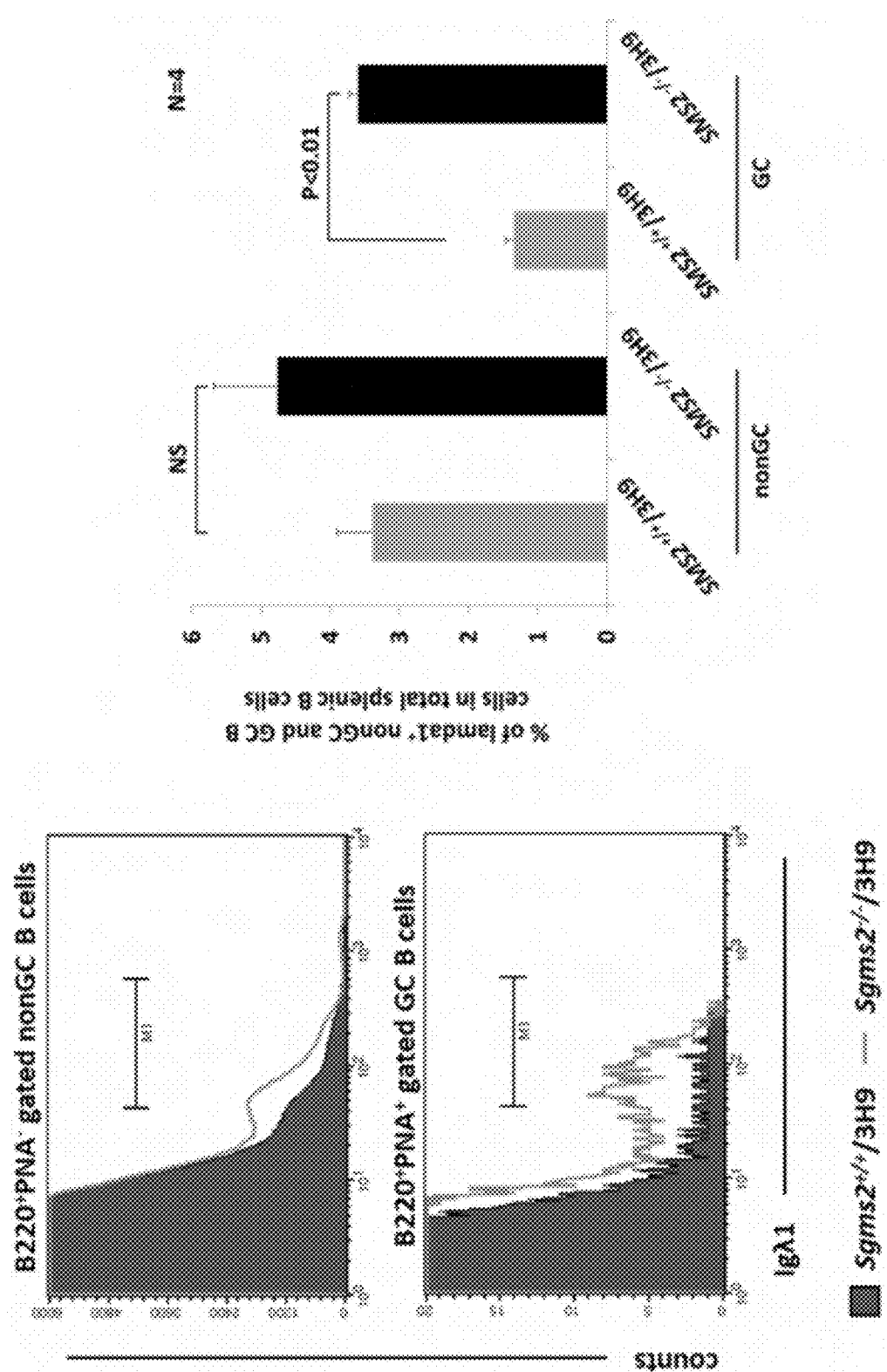
FIG. 2H shows graphical evidence of Flow cytometry analysis of percentages of λ1$^{+}$ (anti-dsDNA) B cells in the GCs of Sgms2$^{-/-}$/3H9 and Sgms2$^{+/+}$/3H9 littermates.

Furthermore, in line with the potential role of SMS2 in regulation of GC B cells' apoptosis, the expression of SMS2, but not SMS1, was highly upregulated in GC B cells. FIG. 2G shows SMS1 and SMS2 mRNA levels in GC B cells and non-GC B (NG) cells isolated from 5 Sgms2$^{+/+}$ mice by RT-PCR analysis. These data supported the hypothesis that in Sgms2$^{-/-}$ mice, defective apoptosis enabled anti-dsDNA B cells to evade B cell tolerance in the GC. This resulted in their consequent activation and differentiation into anti-dsDNA Igs secreting plasma cells. In order to substantiate this hypothesis further, whether SMS2 deficiency could rescue anti-dsDNA B cells otherwise destined for deletion in the GCs of 3H9 mice was evaluated. 3H9 mice carry a transgene encoding a heavy chain that forms anti-dsDNA Ig when it pairs with λ1 light chain. Thus, the fate of anti-dsDNA B cells in 3H9 mice can be tracked by following Igλ1$^+$ B cells. It has been shown that B cell tolerance eliminates Igλ1$^+$ B cells in the GCs of 3H9 mice to block the production of anti-dsDNA Igs. However, as predicated by the hypothesis, the percentage of Igλ1$^+$ B cell in expanded GC B cell pool increased 2-3 fold in Sgms2$^{-/-}$/3H9 mice compared to the percentage of Igλ1$^+$ B cell in non-expanded GC B cell pool in Sgms2$^{+/+}$/3H9 mice. Shown in FIG. 2H is flow cytometry analysis of percentages of Igλ1$^+$ (anti-dsDNA) B cells in the GCs of Sgms2$^{-/-}$/3H9 and Sgms2$^{+/+}$/3H9 littermates. In contrast to GC B cells, in non-GC splenic B cell populations, the difference in the proportion of Igλ1$^+$ B cells between the two strains only slightly increased, but failed to reach statistical significance. Thus, SMS2 deficiency specifically impaired B cell tolerance mechanisms that would otherwise eliminate anti-dsDNA B cells in the GC.

Figure 3A:
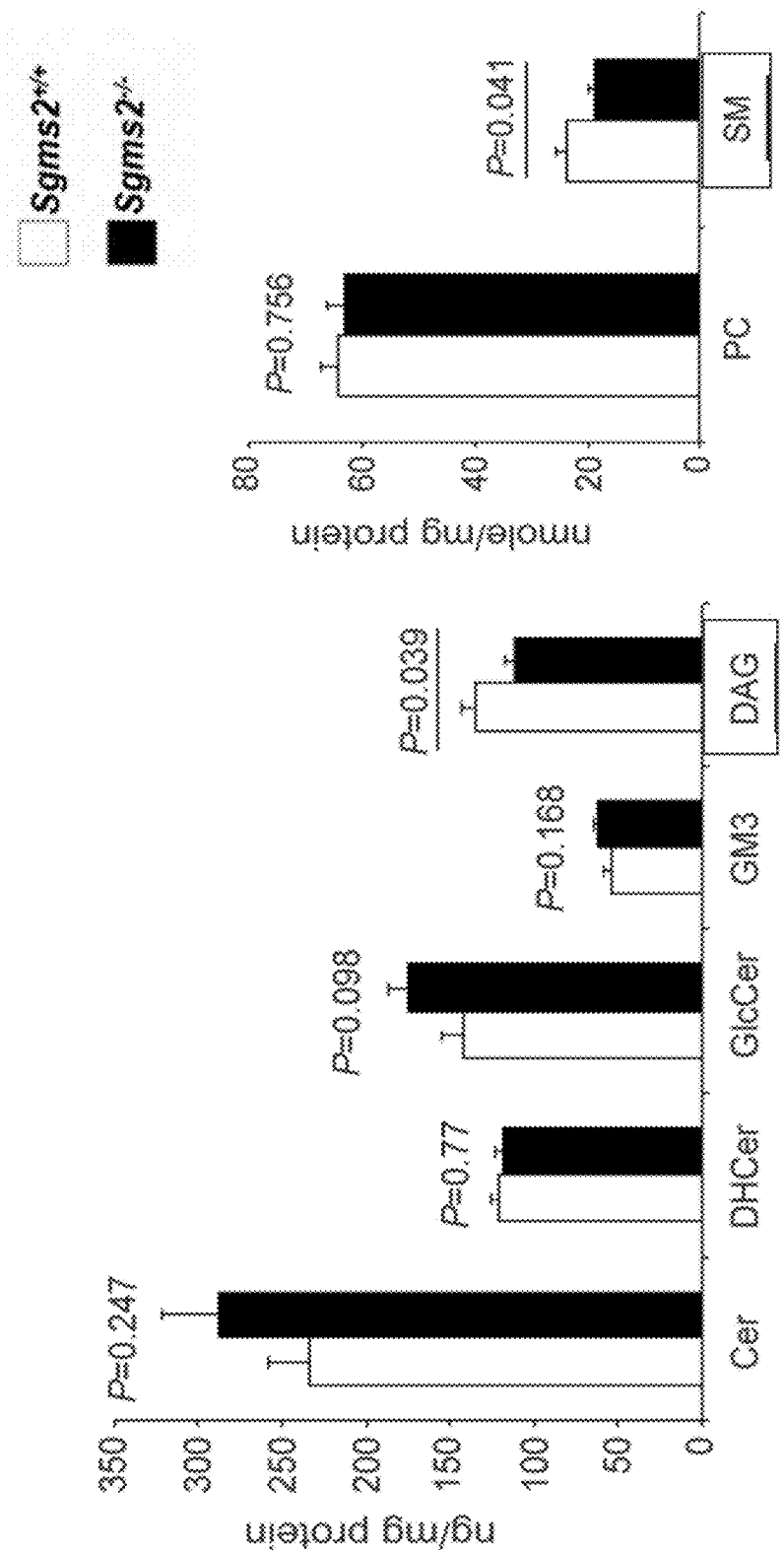
FIG. 3A shows graphical evidence of decreased cellular diacyl glycerol (DAG) and sphingomyelin (SM) but not other sphingolipids in Sgms2$^{-/-}$ B cells, measured by mass spectrometry.
Figure 3B:
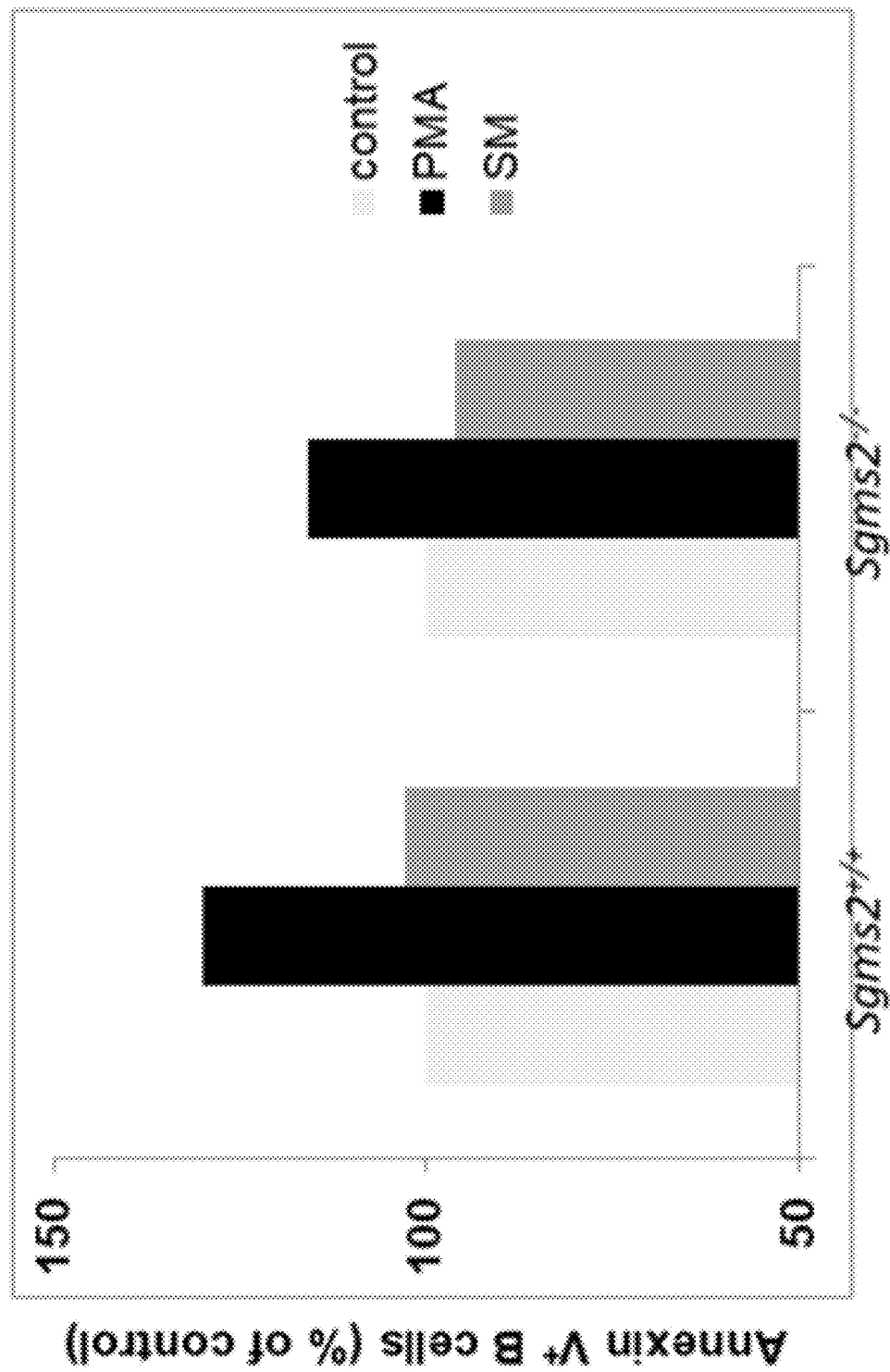
FIG. 3B shows graphical evidence of decreased plasma membrane DAG in Sgms2$^{-/-}$ B cells by ELISA analysis and decreased plasma membrane SM in both Sgms2$^{-/-}$ and Sgms2$^{+/+}$ splenic B cells by lysenin toxicity assay.

To investigate how SMS2 deficiency affected sphingolipid metabolism in ways that could explain the defective apoptosis in Sgms2$^{-/-}$ B cells, relevant sphingolipids in Sgms2$^{-/-}$ B cells were measured. Except for the reduction of SMS's two reaction products, SM and DAG, levels of other sphingolipids, including ceramide, appeared to be unaffected by SMS2 deficiency in B cells. FIG. 3A shows decreased cellular DAG and SM but not other sphingolipids in Sgms2$^{-/-}$ B cells, measured by LC/MS/MS analysis. Interestingly, DAG seemed to regulate B cell apoptosis as we found reduced plasma membrane SM in both Sgms2$^{-/-}$ and Sgms1$^{-/-}$ B cells, but reduced plasma membrane DAG only in Sgms2$^{-/-}$ B cells. FIG. 3B shows decreased plasma membrane DAG in Sgms2$^{-/-}$ B cells (left), and decreased plasma membrane SM in both Sgms2$^{-/-}$ and Sgms1$^{-/-}$ B cells (right). This recalled an untested concept proposed in 1989, suggesting that SMS-derived DAG could activate PKC kinases, and prompted a study of whether SMS2-generated DAG is required for activation of PKCδ, since PKCδ is critical in safeguarding against SLE pathogenesis in both human and mouse. Intriguingly, PKCδ mediates distinct apoptotic pathways in immature and mature B cells. In immature B cells, cytoplasmic PKCδ promotes the activation of ERK-mediated apoptosis in response to BCR signaling whereas in mature B cells, nuclear translocated PKCδ causes apoptosis via phosphorylation of histone 2B.

Figure 3C:
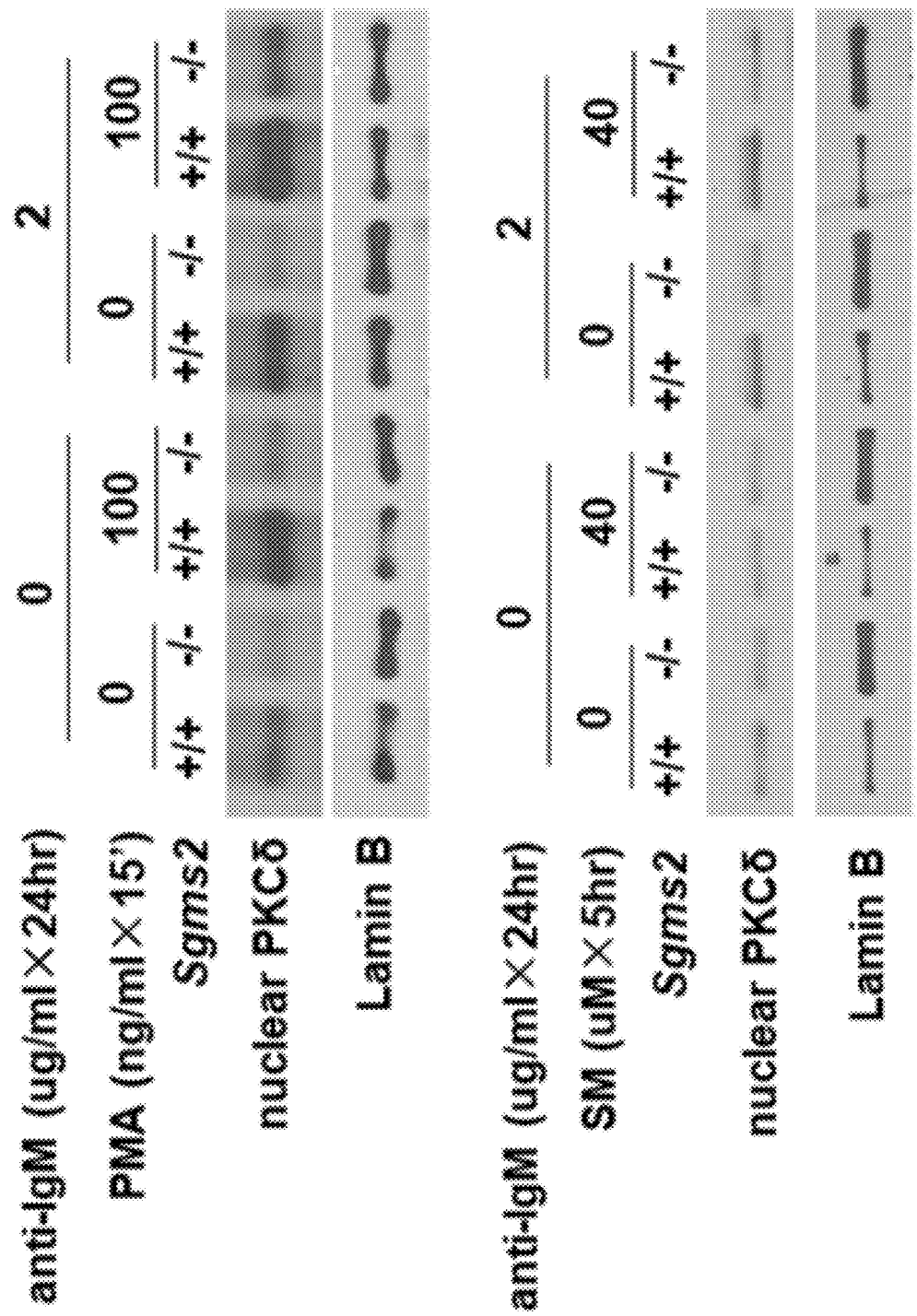
FIG. 3C shows Western blot analysis of reduced nuclear PKCδ in Sgms2$^{-/-}$ splenic B cells, and of PKCδ in Sgms2$^{+/+}$ and Sgms2$^{-/-}$ splenic B cells treated with SM for 24 hr or I3A for 30 min, and lysenin toxicity assay of surface SM levels in Sgms2$^{+/+}$ and Sgms2$^{-/-}$ splenic B cells following SM supplementation.

Generally speaking, PKCs are known to receive DAG on the plasma membrane for their full activation and subsequent subcellular translocation. However, in B cells, the plasma membrane DAG provider that activates PKCδ nuclear translocation is still unknown. Whether SMS2 was the DAG provider for PKCδ activation in mature B cells was therefore tested. In contrast to Sgms2$^{+/+}$ naive B cells, nuclear PKCδ was barely detectable in the Sgms2$^{-/-}$ naive B cells following 24 hr culture. FIG. 3C (left) shows reduced nuclear PKCδ in 24 hr cultured Sgms2$^{-/-}$ B cells analyzed by Western blot. Restoration of surface SM level by SM supplementation could not restore the nuclear PKCδ level in Sgms2$^{-/-}$ B cells (FIG. 3C (left and middle)). However, as shown in FIG. 3C (right), supplementation of a water-soluble DAG analog, ingenol-3-angelate (I3A), increased nuclear PKCδ in both Sgms2$^{+/+}$ and Sgms2$^{-/-}$ B cells cultured for 30 minutes. This DAG analog-dependent effect supported the involvement of SMS2-derived DAG in activation of PKCδ nuclear translocation.

Figure 3D:
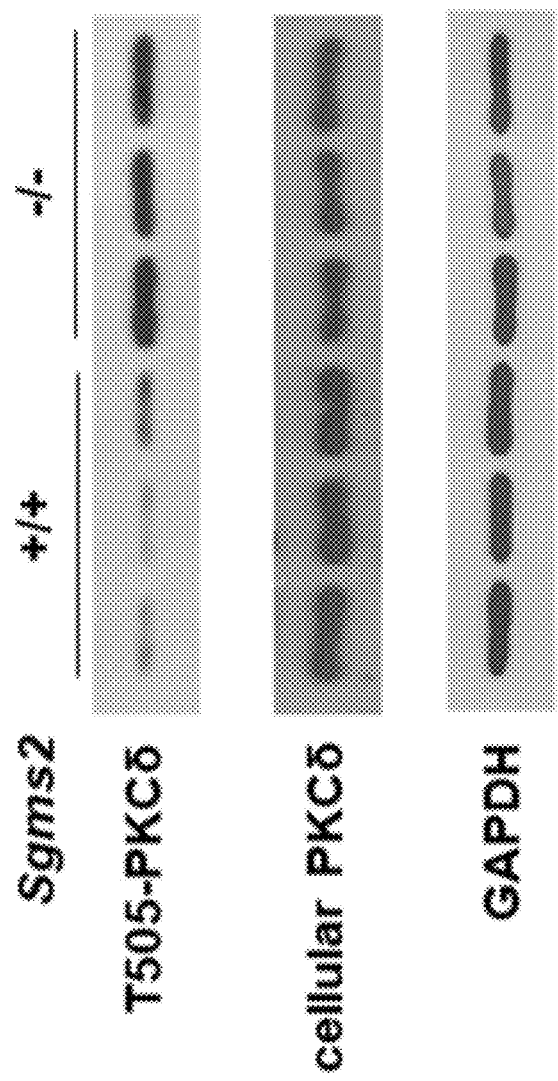
FIG. 3D shows western blot analysis of threonine 505 phosphorylated PKCδ in Sgms2$^{-/-}$ and Sgms2$^{+/+}$ splenic B cells.
Figure 3E:
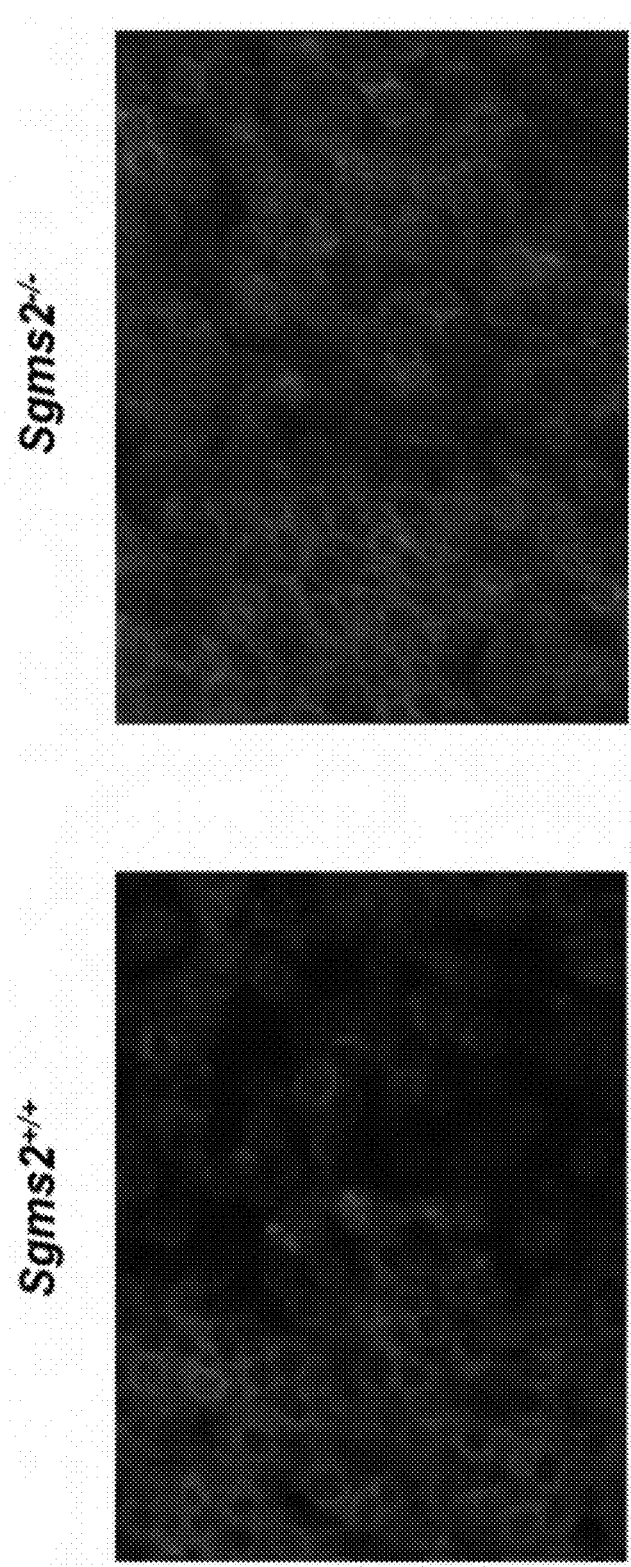
FIG. 3E shows western blot analysis of plasma membrane PKCδ in Sgms2$^{+/+}$ and Sgms2$^{-/-}$ splenic B cells.
Figure 3F:
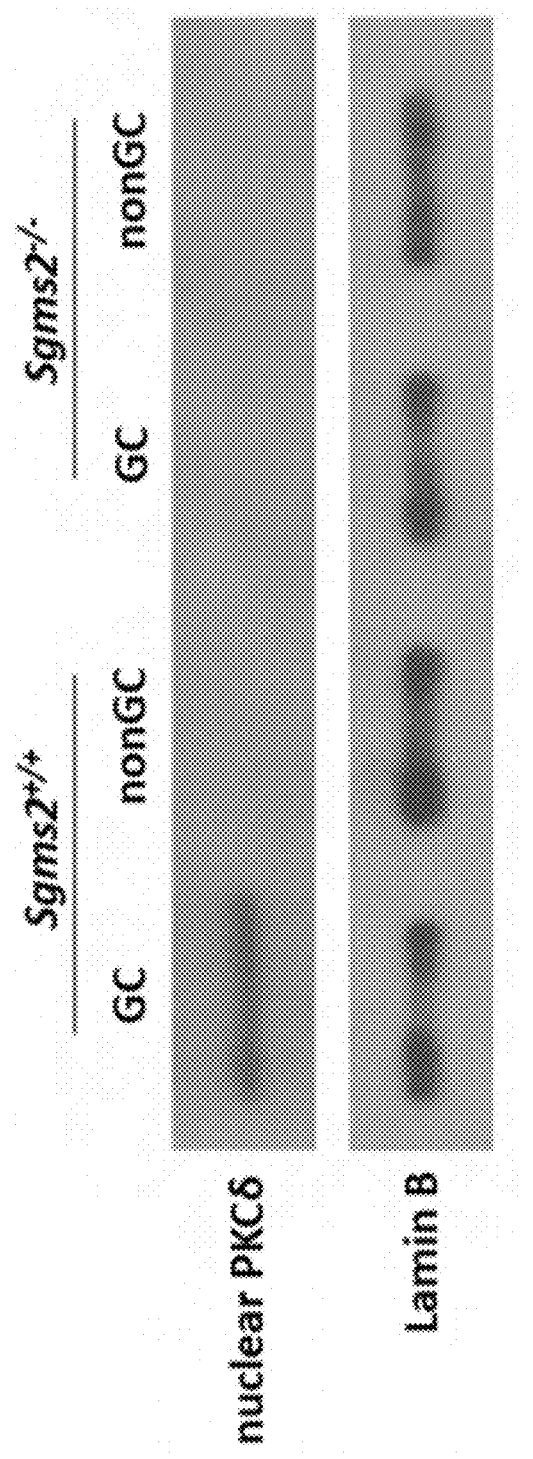
FIG. 3F shows a Western blot analysis of nuclear PKCδ levels in GC and non-GC B cells isolated from Sgms2$^{-/-}$ and Sgms2$^{+/+}$ mice.

Poor nuclear localization of PKCδ in Sgms2$^{-/-}$ B cells was not due to the insufficient PKCδ priming by B cell receptor (BCR), since freshly isolated Sgms2$^{-/-}$ naive B cells had considerably increased threonine 505 phosphorylated PKCδ, a mark of BCR-induced PKCδ priming (FIG. 3D). In keeping with it, Western blot analysis showed increased plasma membrane PKCδ in the isolated Sgms2$^{-/-}$ GC B cells compared to that in the isolated Sgms2$^{+/+}$ GC B cells (FIG. 3E). This was corresponding to the impaired PKCδ nuclear localization in Sgms2$^{-/-}$ GC B cells compared to Sgms2$^{+/+}$ GC B cells. Of note, nuclear PKCδ was also almost undetectable in nuclear extracts from Sgms2$^{+/+}$ and Sgms2$^{-/-}$ non-GC B cells, indicating a requirement of SMS2 for specific PKCδ nuclear translocation in GC B cells. Shown in FIG. 3F is western blot analysis of nuclear PKCδ levels in GC and non-GC (NG) B cells isolated from Sgms2$^{-/-}$ and Sgms2$^{+/+}$ mice.

Figure 4A:
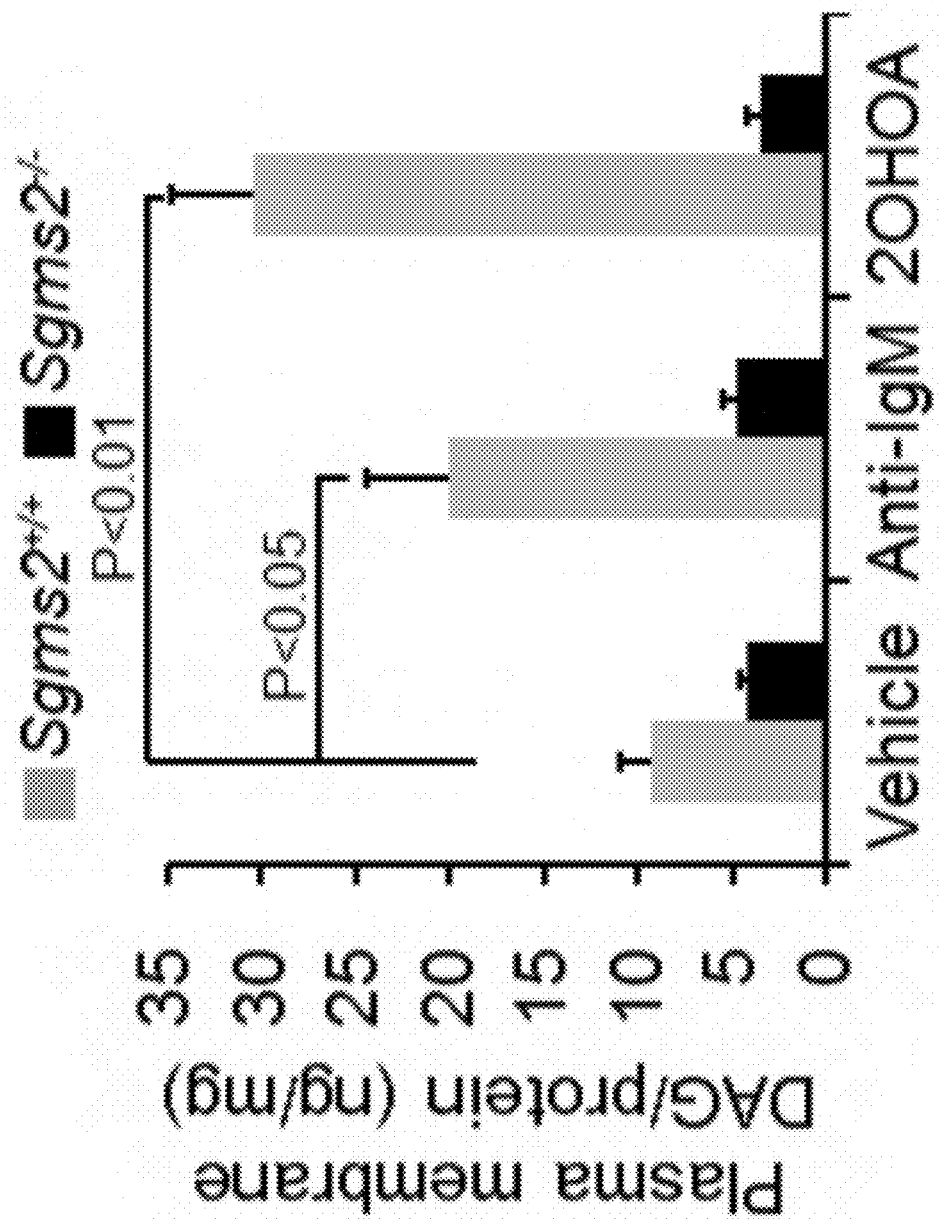
FIG. 4A shows Elisa analysis of plasma membrane DAG levels in anti-IgM or 2OHOA-treated Sgms2$^{+/+}$ B cells and Sgms2$^{-/-}$ B cells.
Figure 4B:
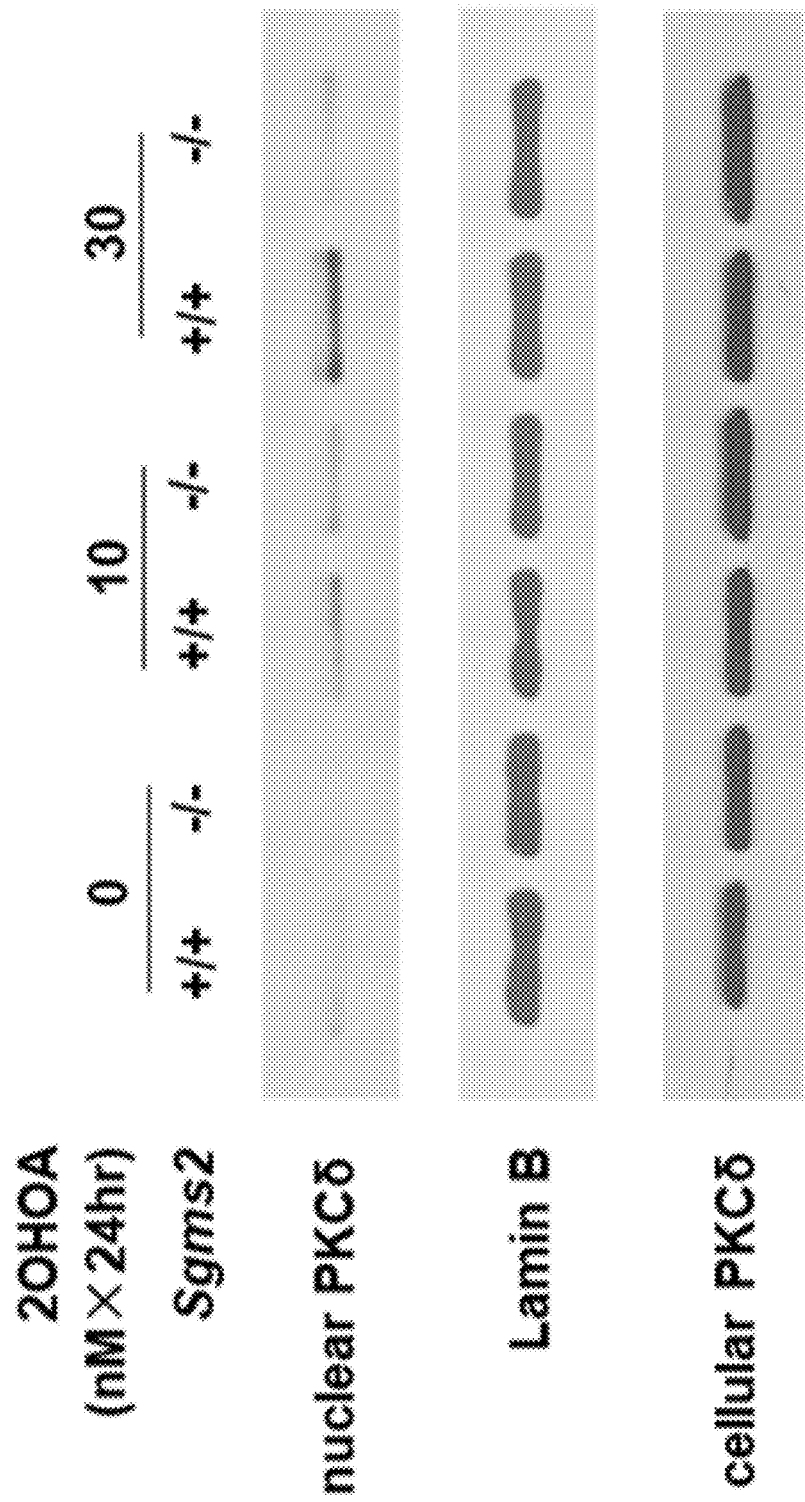
FIG. 4B shows Western blot analysis of nuclear PKCδ in Sgms2$^{-/-}$ and Sgms2+/±splenic B cells treated with 2OHOA.

To further clarify the mechanism that regulates PKCδ activation by SMS2-generated DAG, whether enhancing SMS2 activity could correspondingly increase PKCδ nuclear translocation in cultured Sgms2$^{+/+}$ B cells was tested. Administration of 2-hydroxyoleic acid (2OHOA), an SMS activator, increased SMS2-derived DAG level and PKCδ nuclear translocation in purified Sgms2$^{+/+}$ B cells, but not in Sgms2$^{-/-}$ B cells. FIG. 4A shows Elisa analysis of plasma membrane DAG levels in anti-IgM or 2OHOA-treated Sgms2$^{+/+}$ B cells and Sgms2$^{-/-}$ B cells. FIG. 4B shows western blot analysis of nuclear PKC☐ in Sgms2$^{-/-}$ and Sgms2$^{+/+}$ splenic B cells treated with 2OHOA.

Figure 4C:
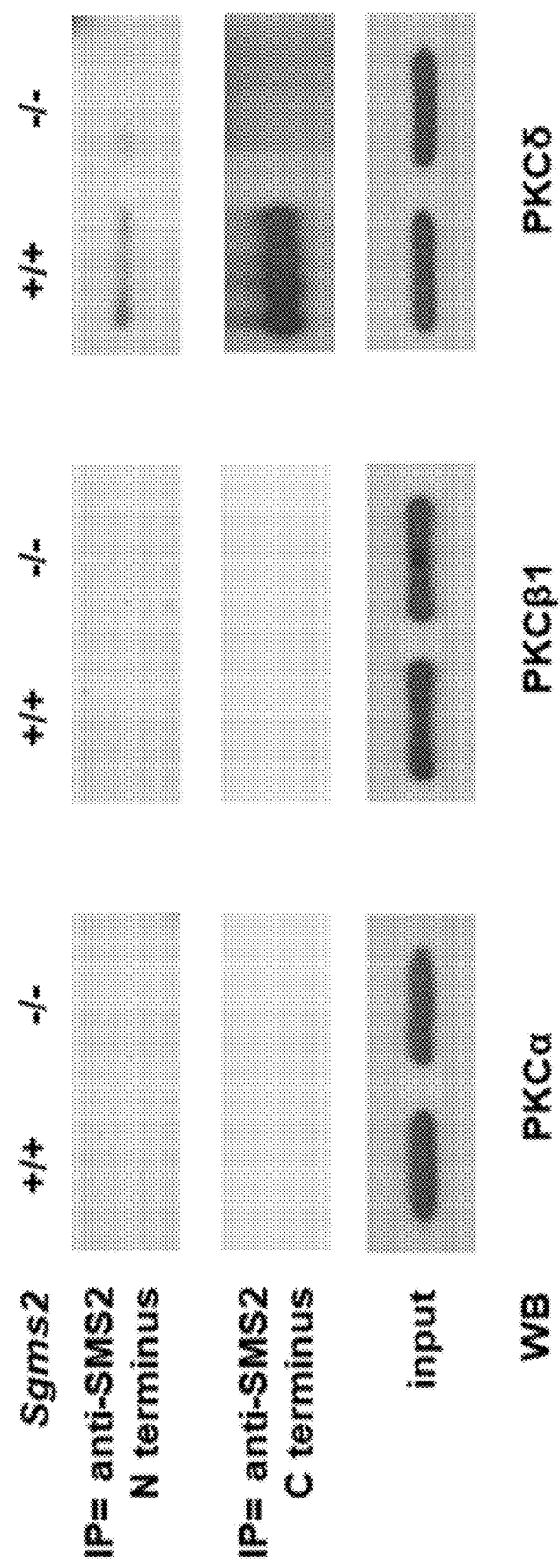
FIG. 4C shows co-immunoprecipitation (CO-IP) analysis of interactions between SMS2 and PKCδ (right panel), but not PKCα (left panel) or PKCβ1 (middle panel), in B cells.

Moreover, in light of the importance of compartmentalized DAG metabolism to orientated signaling events, the possible existence of a SMS2 and PKCδ containing complex that may facilitate DAG signaling was tested. Indeed, co-immunoprecipitation analysis showed that SMS2 formed a complex with PKCδ, but not with other highly expressed PKC isoforms in B cells. FIG. 4C shows CO-IP analysis of interactions between SMS2 and PKCδ in B cells. Protein lysates of isolated Sgms2$^{+/+}$ and Sgms2$^{-/-}$ splenic B cells were immunoprecipitated with anti-SMS2 antibodies. The precipitates were immunoblotted with anti-PKCδ, anti-PKCα and anti-PKCβ antibodies. Results are representative of more than three independent experiments.

Figure 4D:
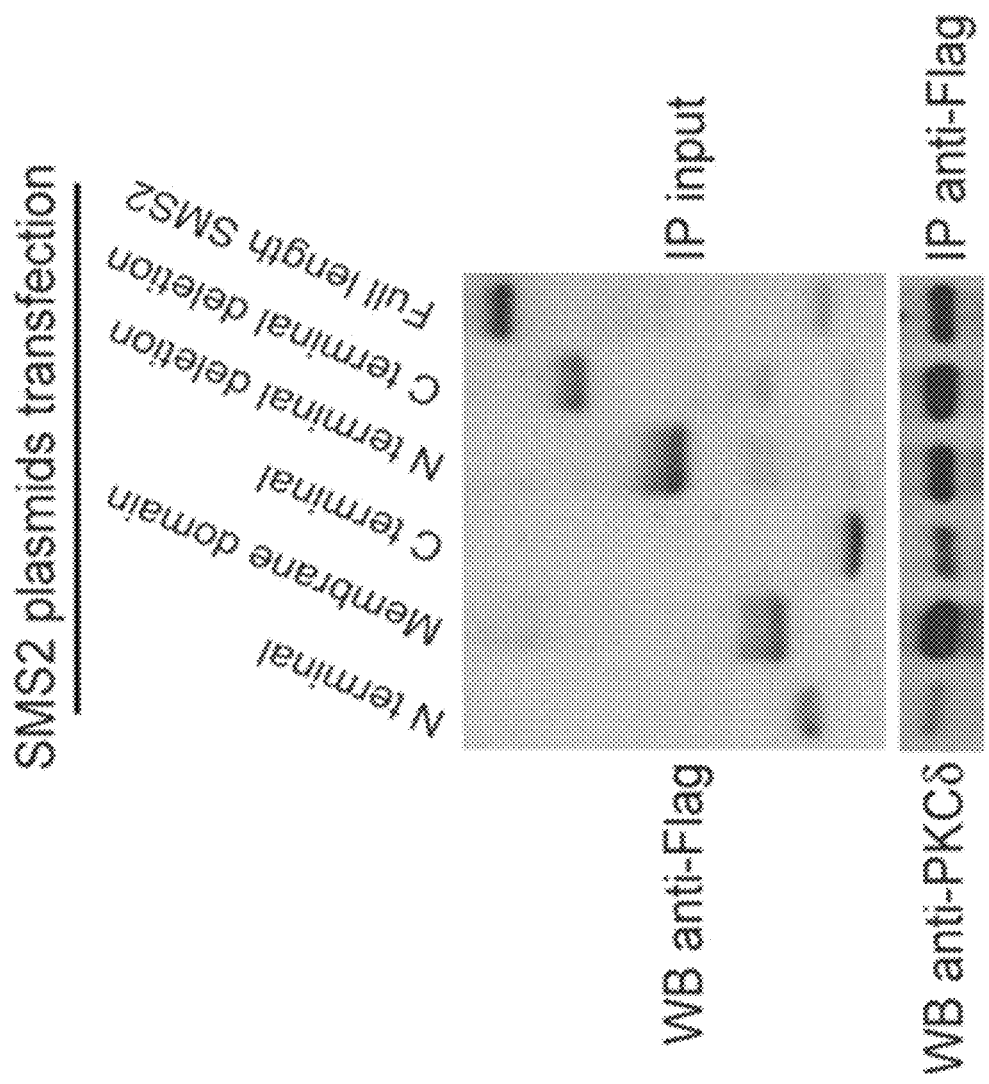
FIG. 4D shows CO-IP analysis of interactions between different SMS2 domains and PKCδ.

A more detailed analysis showed that a membrane domain in SMS2 had the highest affinity to PKCδ. FIG. 4D shows CO-IP analysis of interactions between different SMS2 domains and PKCδ. 293T cells were transfected with plasmid vectors to overexpress FLAG-tagged different SMS2 portions as indicated. Protein lysates from transfected 293T cells were immunoprecipitated with anti-FLAG antibody and then immunoblotted with anti-PKCδ antibody. Sample loading was controlled by inputs of cell lysates. In the light of crystallographic studies of PKCβ, a structurally related PKC, in which the acceptance of DAG required a conformational change in its C terminal caused by its interaction with other protein, the finding of physical interaction between SMS2 and PKCδ also suggested that SMS2 might be required to control the access of DAG to PKCδ. This helped explain the promotion of PKCδ nuclear translocation in Sgms2$^{+/+}$ B cells, but not in Sgms2$^{-/-}$ B cells by PMA, another DAG analog (FIG. 3E). Thus, SMS2 is a critical and direct PKCδ activator in mature B cells.

Figure 5:
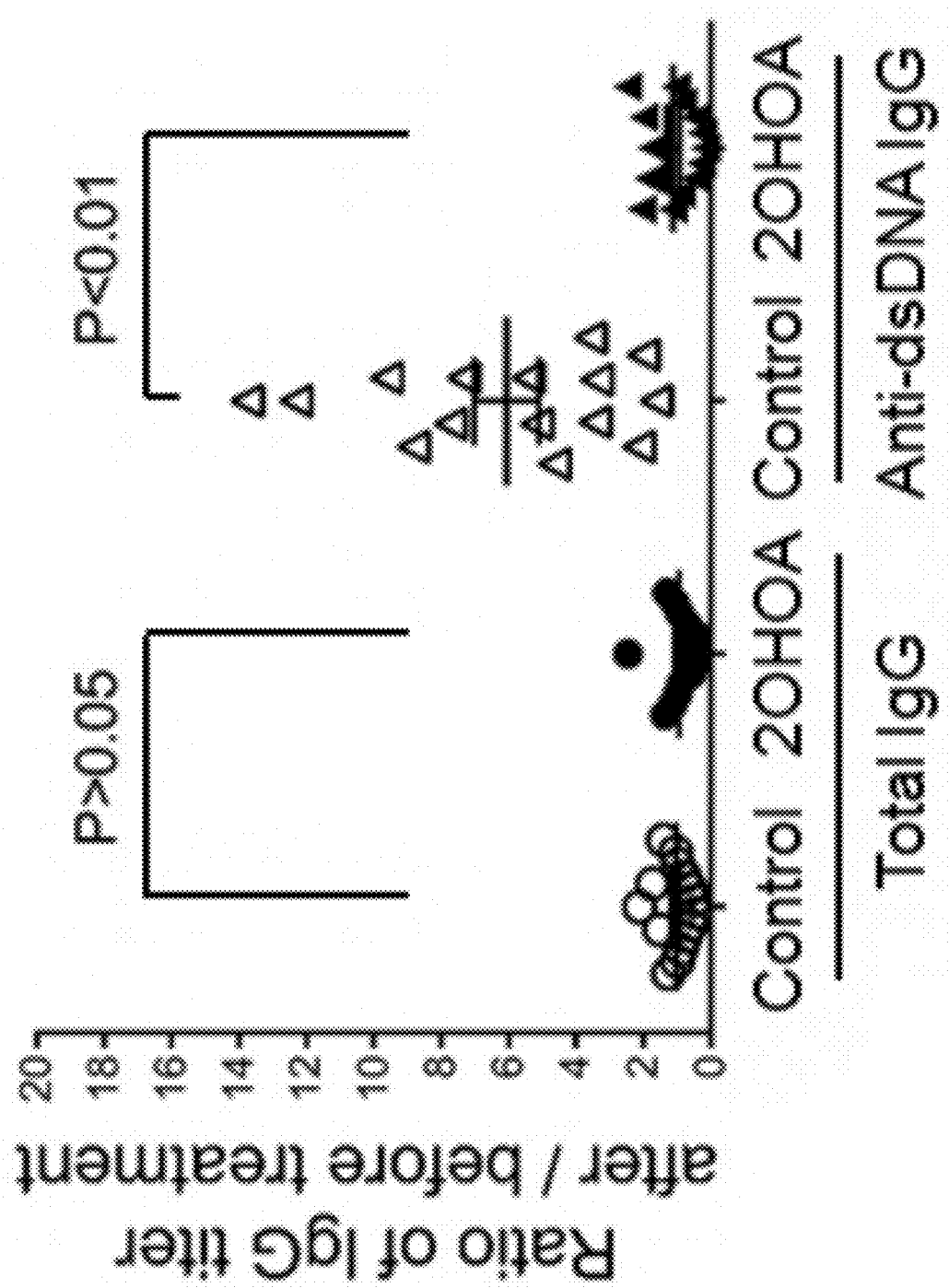
FIG. 5 shows effects of 2OHOA treatment on the total IgG and anti-dsDNA IgG levels in NZBWF1 mice (a spontaneous SLE mouse model).

Given that PKCδ nuclear translocation was promoted by enhancing SMS2 activity with 2OHOA, whether this drug could be adopted to strengthen B cell tolerance in NZBWF1 mice that spontaneously develop SLE due to impaired tolerance caused by multiple genetic variants other than Sgms2 or Prkcd was examined. Remarkably, the expected increase in titers of anti-dsDNA IgGs in the sera of NZBWF1 mice over the same time frame as sham treated mice was impeded by 2OHOA treatment. Notably, when 2OHOA was applied at an optimized dosage (400 mg/kg/day), its effect could be specific to the autoantibody and not a reflection of a general inhibition of B cell activation, given that it occurred without reducing the total serum IgG titers. FIG. 5 shows female NZBWF1 mice received an oral gavage of 2OHOA at the dose of 400 mg/kg per day for a period of four weeks. This treatment started when the mouse serum anti-dsDNA IgG level reached the levels between 1,000 ng/ml and 30,000 ng/ml. The titers of serum total IgG and anti-dsDNA IgG were measured by ELISA. Shown in the graph are ratios of the IgG titers after treatment to the titers before treatment. Mann-Whitney test (2 tailed) was used to calculate p values, SEMs, and other parameters as shown in the graph and table. Data represents the results of 15 2OHOA-treated and 10 empty vehicle-treated mice. This in vivo result suggests a new potential therapeutic strategy for SLE patients by targeting SMS2.

Figure 6A:
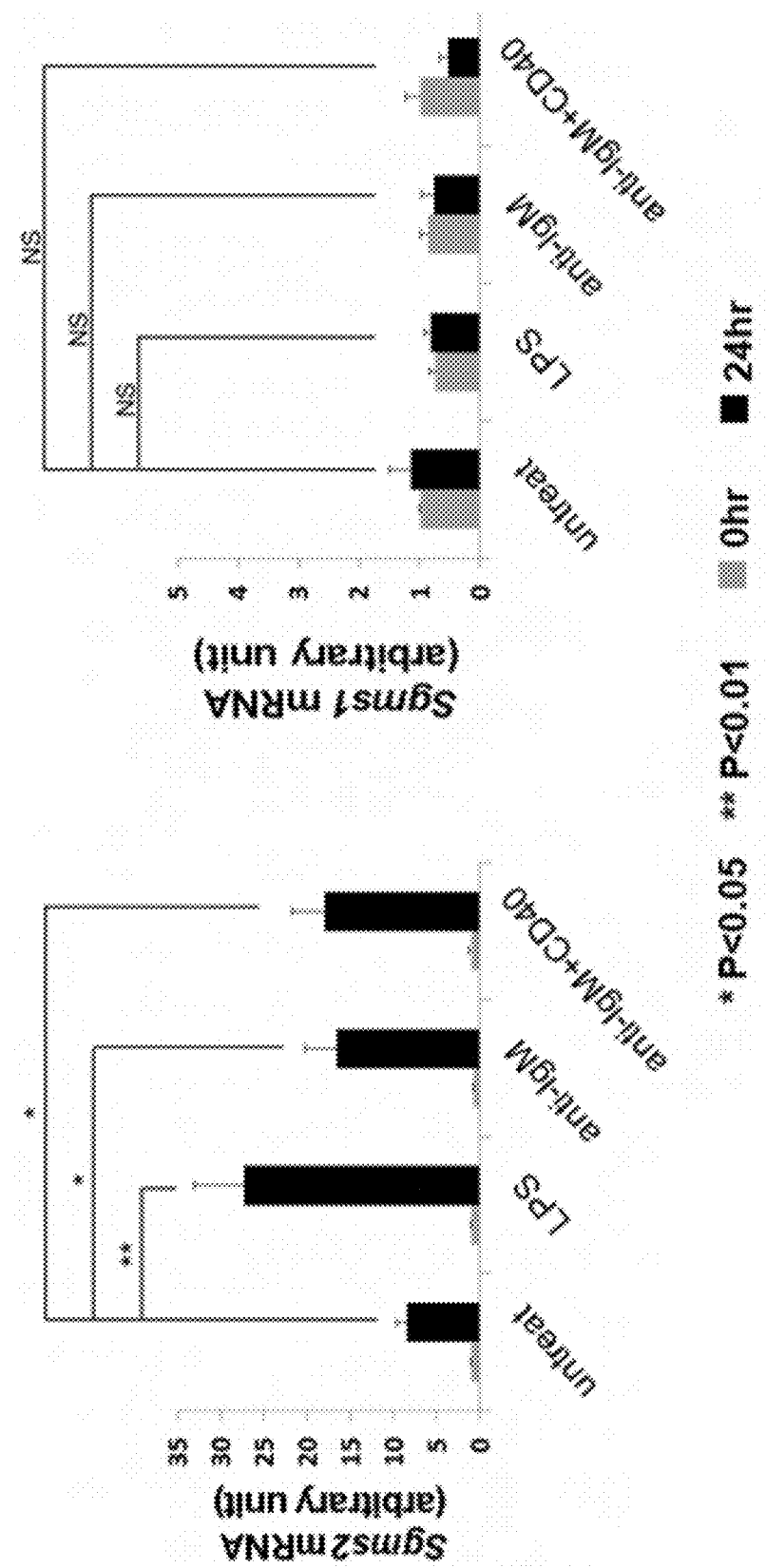
FIG. 6A shows bar graphs of real-time PCR analysis demonstrating upregulated SMS2 (but not SMS1) expression in response to B-cell receptor (BCR) signaling.
Figure 6B:
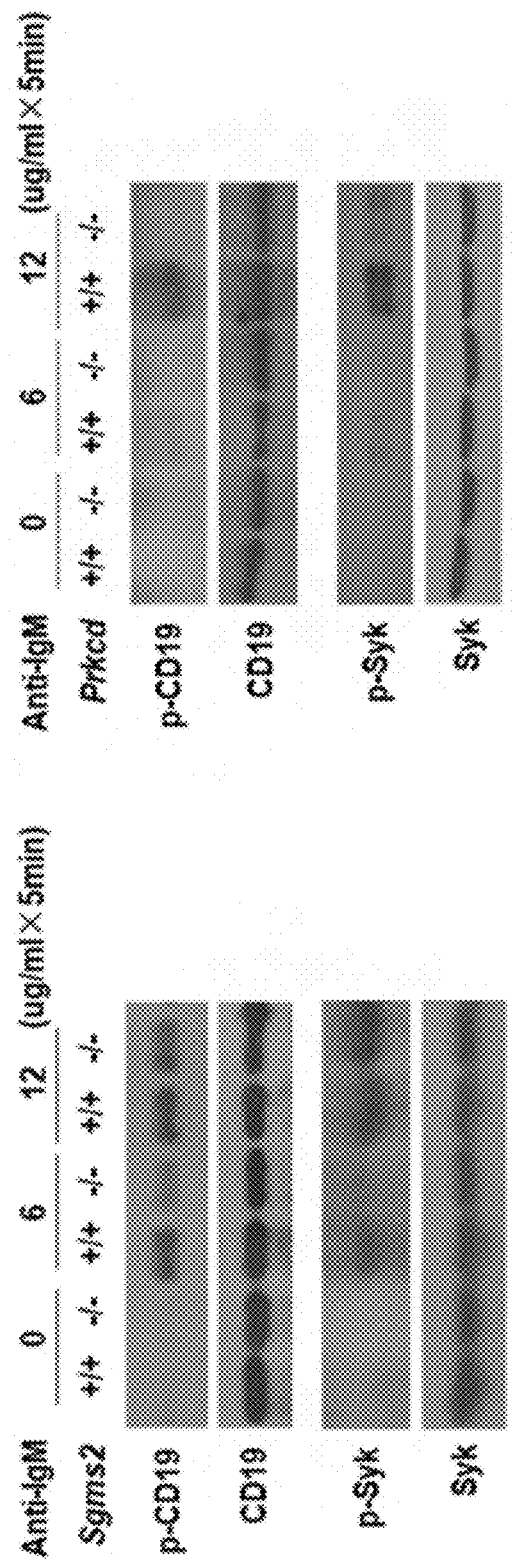
FIG. 6B is a western blot analysis of phosphorylated CD19, total CD19, phosphorylated Syk and total Syk in Sgms2$^{-/-}$ B cells and Prkcd$^{-/-}$ B cells.

SMS2-regulated PKCδ nuclear translocation appeared to be triggered by BCR stimulation since that BCR stimulation increased SMS2 activity and expression (FIG. 4A, 6A), as well as PKCδ nuclear translocation in cultured B cells (FIG. 3C, 3E). FIG. 6A shows upregulated SMS2 expression in response to BCR signaling. Real-time RT-PCR analysis of SMS1 and SMS2 mRNA levels in B cells with or without indicated BCR stimuli. Data are representative of 4 independent experiments. Student's t-test was used in the analysis.

Figure 6C:
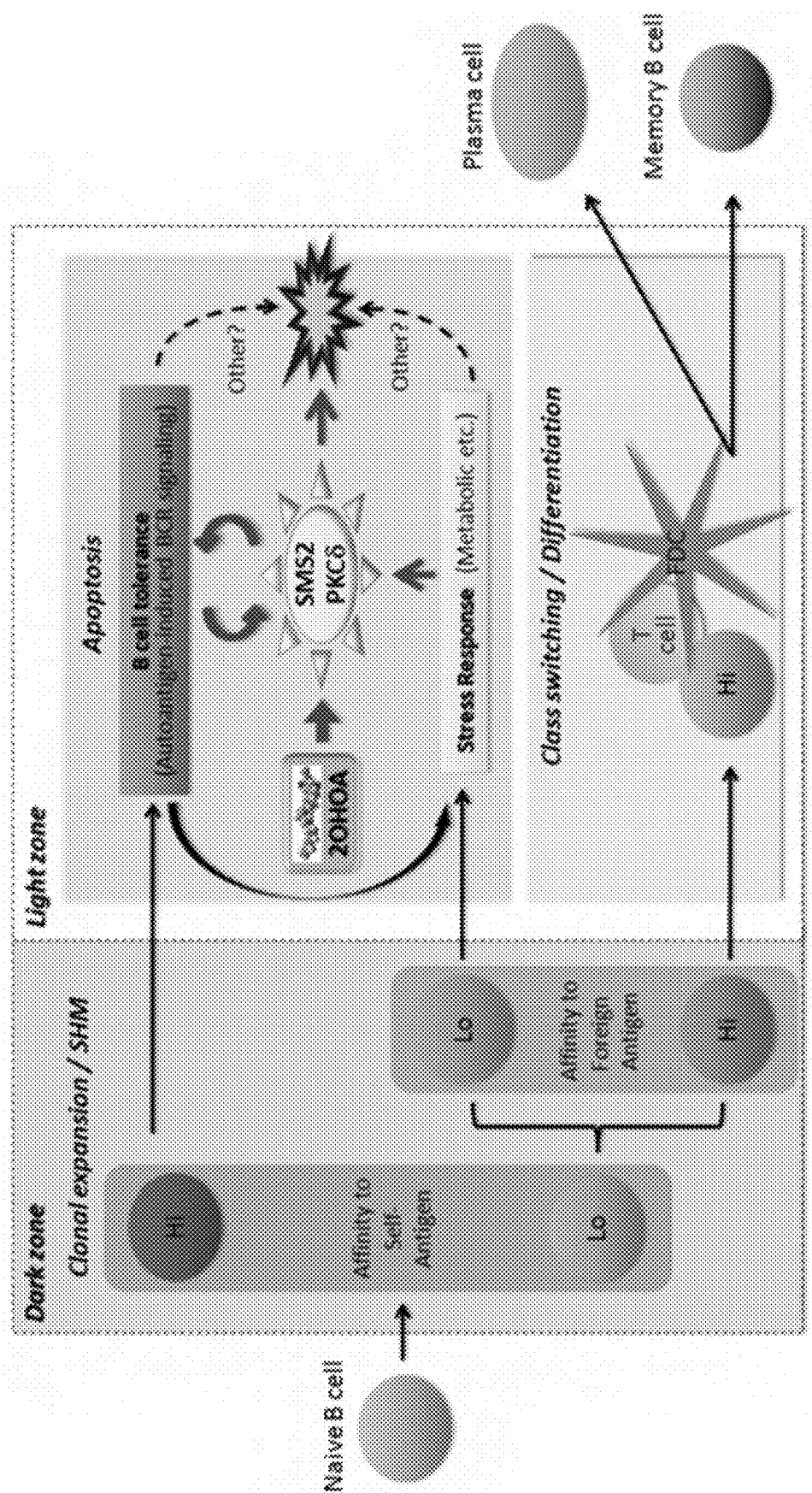
FIG. 6C is a diagrammatic representation of a model of SMS2-mediated B cell tolerance in the GC.

These data therefore collectively suggest the existence of a SMS2-regulated PKC activation that activates apoptosis in anti-dsDNA GC B cells. This SMS2-mediated B cell tolerance in the GC could be activated by BCR signaling and metabolic stress in GC B cells. FIG. 6C shows a model of SMS2-mediated B cell tolerance in the GC.

What is claimed is:

1. A method of treating lupus in a human subject in need of such treatment, wherein the lupus is characterized by presence of serum anti-dsDNA antibodies, comprising
administering to the subject 2-hydroxyoleic acid in an amount effective to reduce serum levels of anti-double stranded DNA antibodies in the subject.

2. The method of claim 1, wherein the subject exhibits symptoms of systemic lupus erythematosus.

3. The method of claim 1 wherein the subject exhibits symptoms of lupus nephritis.

4. The method of claim 1, further comprising administering one or more second compound to the subject and the one or more second compound is selected from an immunosuppressant compound, a corticosteroid, a non-steroidal anti-inflammatory compound, an anti-malarial compound, an anti-B-cell-specific surface antigen antibody, and anti-BAFF antibody.

5. The method of claim 2, further comprising administering one or more second compound to the subject and the one or more second compound is selected from an immunosuppressant compound, a corticosteroid, a non-steroidal anti-inflammatory compound, an anti-malarial compound, an anti-B-cell-specific surface antigen antibody, and anti-BAFF antibody.

6. The method of claim 3, further comprising administering one or more second compound to the subject and the one or more second compound is selected from an immunosuppressant compound, a corticosteroid, a non-steroidal anti-inflammatory compound, an anti-malarial compound, an anti-B-cell-specific surface antigen antibody, and anti-BAFF antibody.

7. A method of treating lupus nephritis in a human subject in need of such treatment, wherein the lupus nephritis is characterized by presence of serum anti-dsDNA antibodies comprising
administering to the subject 2-hydroxyoleic acid in an amount effective to reduce serum levels of anti-double stranded DNA antibodies in the subject.

8. The method of claim 7 wherein the subject exhibits symptoms of lupus nephritis.

9. The method of claim 7, further comprising administering one or more second compound to the subject and the one or more second compound is selected from an immunosuppressant compound, a corticosteroid, a non-steroidal anti-inflammatory compound, an anti-malarial compound, an anti-B-cell-specific surface antigen antibody, and anti-BAFF antibody.

10. The method of claim 8, further comprising administering one or more second compound to the subject and the one or more second compound is selected from an immunosuppressant compound, a corticosteroid, a non-steroidal anti-inflammatory compound, an anti-malarial compound, an anti-B-cell-specific surface antigen antibody, and anti-BAFF antibody.

11. A method of treating systemic lupus erythematosus in a human subject in need of such treatment, comprising
administering to the subject 2-hydroxyoleic acid in an amount effective to reduce serum levels of anti-double stranded DNA antibodies in the subject.

12. The method of claim 11, wherein the subject exhibits symptoms of systemic lupus erythematosus.

13. The method of claim 11, further comprising administering one or more second compound to the subject and the one or more second compound is selected from an immunosuppressant compound, a corticosteroid, a non-steroidal anti-inflammatory compound, an anti-malarial compound, an anti-B-cell-specific surface antigen antibody, and anti-BAFF antibody.

14. The method of claim 12, further comprising administering one or more second compound to the subject and the one or more second compound is selected from an immunosuppressant compound, a corticosteroid, a non-steroidal anti-inflammatory compound, an anti-malarial compound, an anti-B-cell-specific surface antigen antibody, and anti-BAFF antibody.

\* \* \* \* \*